(12) United States Patent
Wu

(10) Patent No.: US 7,935,684 B2
(45) Date of Patent: May 3, 2011

(54) METHOD FOR TREATING ALLERGIC DISEASES

(75) Inventor: Rong-Tsun Wu, Taipei (TW)

(73) Assignee: National Yang-Ming University, Taipei (TW)

( * ) Notice: Subject to any disclaimer, the term of this patent is extended or adjusted under 35 U.S.C. 154(b) by 286 days.

(21) Appl. No.: 12/177,728

(22) Filed: Jul. 22, 2008

(65) Prior Publication Data

US 2010/0022470 A1 Jan. 28, 2010

(51) Int. Cl.
*A61K 31/715* (2006.01)
(52) U.S. Cl. .......................................... 514/54; 536/128
(58) Field of Classification Search ........................ None
See application file for complete search history.

(56) References Cited

U.S. PATENT DOCUMENTS 6,586,403 B1 * 7/2003 Mathison et al. ............... 514/18
2006/0251739 A1 11/2006 Wu

OTHER PUBLICATIONS

Mizushima, Y. et al "Oral adminstration of leflunomide . . . " J. Pharmacol. Exp. Ther. (1999) vol. 288, No. 2, pp. 849-857.*
Zha et al., "Structure identification of a new immunostimulating polysaccharide from the stems of *Dendrobium huoshanense*" Carbohydrate Polymers 69 (2007) 86-93.
Ko et al., "Enhancement of ATP generation capacity, antioxidant activity and immunomodulatory activities by Chinese Yang and Yin tonifying herbs" Chinese Medicine 2007, 2:3.
Zhao et al., "Antioxidant and Anti-hyperglycemic Activity of Polysaccharide Isolated from *Dendrobium chrysotoxum* Lindl" Journal of Biochemistry and Molecular Biology, vol. 40, No. 5, Sep. 2007, pp. 670-677.
Clark, "*Omalizumab in the Treatment of Allergic Respiratory Disease*", Journal of Asthma, 43:87-93, 2006.
Cooper, "*Intestinal Worms and Human Allergy*", Parasite Immunology, 2004, 26, 455-467.
Holgate, "*The Anti-inflammatory Effects of Omalizumab Confirm the Central Role of IgE in Allergic Inflammation*", 2005 American Academy of Allergy, Asthma and Immunology, J. Allergy Clin Immunol, vol. 115, No. 4.
Lilly, "*Diversity of Asthma: Evolving Concepts of Pathophysiology and Lessons from Genetics*", 2005 American Academy of Allergy, Asthma and Immunology doi:10.1016/j.jaci.2005.01.028.
Menzies-Gow, "*Eosinophil Chemokines and Chemokine Receptors: Their Role in Eosinophil Accumulation and Activation in Asthma and Potential as Therapeutic Targets*", Journal of Asthma, 38(8), 605-613 (2001).
Milgrow, "*Treatment of Allergic Asthma With Monoclonal Anti-IgE Antibody*", New England Journal of Medicine, vol. 341, No. 26, Dec. 23, 1999.
Perkins, "*IL-4 Induces IL-13-independent Allergic Airway Inflammation*", J. Allergy Clin Immunol, vol. 118, No. 2, (2006).
Platts-Mills, "*The Role of Immunoglobulin E in Allergy and Asthma*", American Journal of Respiratory and Critical Care Medicine, vol. 164, 2001.
Satoh, "Specific Inhibition of $Na^+,K^+$ ATPase Activity by Atractylon, a Major Component of Byaku-jutsu, by Interaction with Enzyme in the $E_2$ State", Biochemical Pharmacology, vol. 51, pp. 339-343, 1996. Copyright © 1996 Elsevier Science Inc.
Odemuyiwa, "*Cutting Edge: Human Eosinophils Regulate T Cells Subset Selection through Indoleamine 2,3-Dioxygenase*", The Journal of Immunology, 2004, 5909-5913.
Rothenberg, "*Mechanisms of Disease*", The New England Journal of Medicine, May 28, 1998, 1592-1600.
Sarinho, "*Anti-IgE monoclonal antibody for the treatment of asthma and other manifestations related to allergic diseases*", Jornal de Pediatrai—vol. 82, No. 5 (Suppl), 2006.
Schopf, "*Differential Moducation of Allergic Eye Disease by Chronic and Acute Ascaris Infection*", Investigative Opthalmology & Visual Science, Aug. 2005, vol. 46, No. 8.
Sumi, "*Thymus-Derived CD4+CD25+T Cells Suppress the Development of Murine Allergic Conjunctivities*", Int Arch Allergy Immunol 2007; 143:376-281.
Wagelie-Steffen, "*Biologic Therapies for the Treatment of Asthma*", Clin Chest Med 27 (2006) 133-147.
Walsh, "*Eosinophil Granule Proteins and their Role in Disease*", Current Opinion in Hematology 2001, 8:28-33.
Yamaguchi, "*Antioxidant Activity of the Extracts from Fruiting Bodies of Cultured Cordyceps Sinensis*", Phytotherapy Research, Rphyother, Res. 14, 647-649 (2000).
Zhang, "*Asthmalike biphasic airway responses in Brown Norway rats sensitized by dermal exposure to dry trimellitic anhydride power*", J. Allergy Clin Immunol, vol. 113, No. 2, (2004).
Zhao, "*Antioxidant and Anti-hyperglycemic Activity of Polysaccharide Isolated from Dendrobium chrysotoxum Lindl*", Journal of Biochemistry and Molecular Biology, vol. 40, No. 5, Sep. 2007, pp. 670-677.

\* cited by examiner

*Primary Examiner* — Leigh C Maier
(74) *Attorney, Agent, or Firm* — Hsiu-Ming Saunders; Intellectual Property Connections, Inc.

(57) ABSTRACT

The present invention relates to use of polysaccharides obtained from *Dendrobium* for treating an allergic disease or for reducing airway-remodeling caused by inflammation.

20 Claims, 21 Drawing Sheets

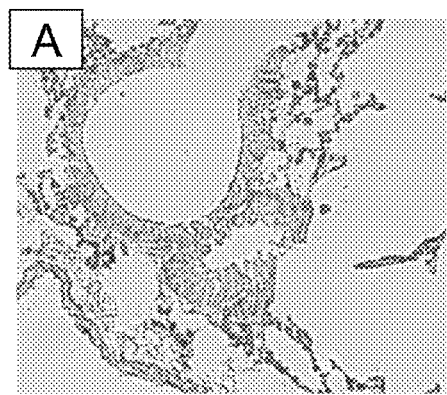 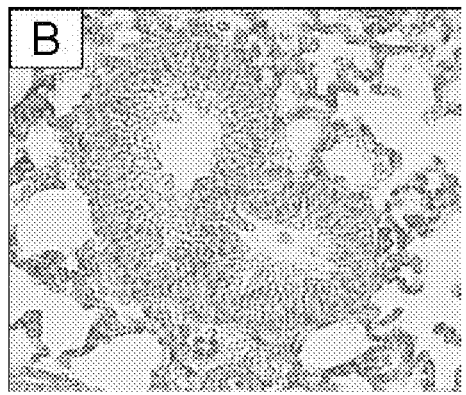
Fig. 4A Fig. 4B
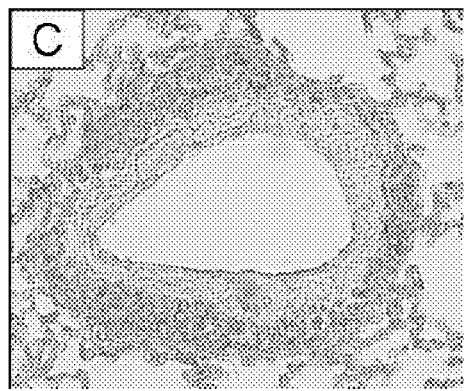 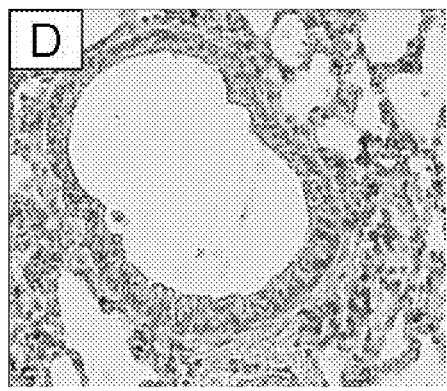
Fig. 4C Fig. 4D
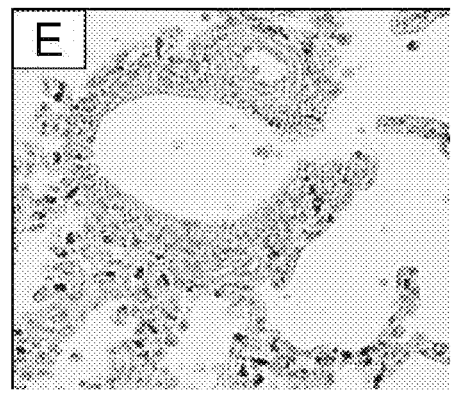
Fig. 4E

SEQUENCE LISTING

<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
gtgggccgcc ctaggcacca                                               20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
tggccttagg gttcaggggg                                               20

<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3
ggagctgagc aacatgacac a                                             21

<210> SEQ ID NO 4
<211> LENGTH: 21
<212> TYPE: DNA
<213> ORGANISM: Artificial
<220> FEATURE:
<223> OTHER INFORMATION: primer

<400> SEQUENCE: 4
ggtcctgtag atggcattgc a                                             21

<210> SEQ ID NO 5
<211> LENGTH: 24
<212> TYPE: DNA
<213> ORGANISM: Artificial
<220> FEATURE:
<223> OTHER INFORMATION: primer

<400> SEQUENCE: 5
gggcagtaac ttccatctgt ctcc                                          24

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
cacttcttct tggggtcagc                                               20

<210> SEQ ID NO 7
<211> LENGTH: 26
<212> TYPE: DNA
<213> ORGANISM: Artificial
<220> FEATURE:
<223> OTHER INFORMATION: primer

<400> SEQUENCE: 7
ttatgcagac tgtgtcctgg caactg                                        26

<210> SEQ ID NO 8
<211> LENGTH: 27
<212> TYPE: DNA

```
-continued

<213> ORGANISM: Artificial
<220> FEATURE:
<223> OTHER INFORMATION: primer

<400> SEQUENCE: 8
tttccagcca gacagatata tgcggag                                      27

<210> SEQ ID NO 9
<211> LENGTH: 19
<212> TYPE: DNA
<213> ORGANISM: Artificial
<220> FEATURE:
<223> OTHER INFORMATION: primer

<400> SEQUENCE: 9
gctccagaag gccctcaga                                               19

<210> SEQ ID NO 10
<211> LENGTH: 19
<212> TYPE: DNA
<213> ORGANISM: Artificial
<220> FEATURE:
<223> OTHER INFORMATION: primer

<400> SEQUENCE: 10
agctttccct ccgcattga                                               19

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
tgcaagtact agtacggatg gggc                                         24

<210> SEQ ID NO 12
<211> LENGTH: 24
<212> TYPE: DNA
<213> ORGANISM: Artificial
<220> FEATURE:
<223> OTHER INFORMATION: primer

<400> SEQUENCE: 12
ggacttcttg tgccatttcc tgag                                         24
```

US 7,935,684 B2

METHOD FOR TREATING ALLERGIC DISEASES

TECHNICAL FIELD

This invention relates to treating allergic diseases with polysaccharides isolated from *Dendrobium*.

BACKGROUND

*Dendrobium* is a genus of tropical orchids widely distributed in Asia, Europe, and Australia. Some of its species have a long history of use in traditional Chinese medicine for improving skin quality and vision. It has also been reported that *Dendrobium* exhibits antioxidation, anti-inflammation, and immune-regulation activities. See Satoh et al., *Biochem. Pharmacol.* 51: 339-343, 1996; Yamaguchi et al., *Cordyceps sinensis. Phytoher. Res.* 14: 647-649, 2000; Zhao et al., *J. Biochem. Molecular Bio.* 40(5): 670-677, 2007; and US 20060251739.

SUMMARY OF THE INVENTION

This invention is based on the unexpected discoveries that polysaccharides prepared from *Dendrobii Herba* (i.e., *Dendrobium* stem) are effective in treating allergic diseases such as asthma, pollen allergy, and atopic dermatitis.

Accordingly, the present invention provides a method of treating an allergic disease (e.g., asthma, pollen allergy, allergic conjunctivitis, or atopic determitis) by administering (e.g., orally) to a subject an effective amount of polysaccharides prepared from *Dendrobii Herba*.

The term "treating" as used herein refers to the application or administration of a composition including one or more active agents to a subject, who has an allergic disease, a symptom of the allergic disease, or a predisposition toward the allergic disease, with the purpose to cure, heal, alleviate, relieve, alter, remedy, ameliorate, improve, or affect the disease, the symptoms of the disease, or the predisposition toward the disease. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

In one example, the polysaccharides used to practice the method of this invention are prepared by a process including at least the following five steps: i. soaking a first *Dendrobii Herba* preparation in a first alcohol (e.g., methanol, ethanol, or a mixture thereof), ii. removing the first alcohol to produce a second *Dendrobii Herba* preparation; iii. extracting the second *Dendrobii Herba* preparation with water (i.e., pure water or a suitable water-containing solvent) to obtain an aqueous solution; (iv) mixing the aqueous solution with a second alcohol (e.g., 50% ethanol by volume) to allow precipitation of polysaccharides, and (v) collecting the precipitated polysaccharides.

The present invention further provides a method of reducing airway-remodeling resulted from inflammation by administrating to a subject in need thereof an effective amount of the polysaccharides described above.

Also within the scope of this invention is use of the polysaccharides described herein for treating an allergic disease or reducing inflammation-induced airway-remodeling, or for the manufacture of a medicament for these treatments.

The details of one or more embodiments of the invention are set forth in the description below. Other features, objects, and advantages of the invention will be apparent from the description and from the claims.

BRIEF DESCRIPTION OF THE DRAWINGS

In the drawings:

FIG. 4 is a diagram showing the Haematoxylin and Eosin (H&E) Staining of the lung sections of the mice in Example 2. The lung tissue was removed from mice, then fixed with 10% formalin. Three days later, the lung was subsequently embedded in paraffin and cut into 5 μm-thick sections. Part A to E represented the five groups in Example 2: the normal group (healthy mice as negative control), the control group (mice was sensitized with OVA but without *Dendrobii Herba* treatment), the treatment groups sensitized with OVA were fed with a dose of 10 mg/kg/day (n=8), 30 mg/kg/day (n=8) and 90 mg/kg/day (n=8), respectively. Magnification is 100×.

DETAILED DESCRIPTION OF THE INVENTION

Figure 1:
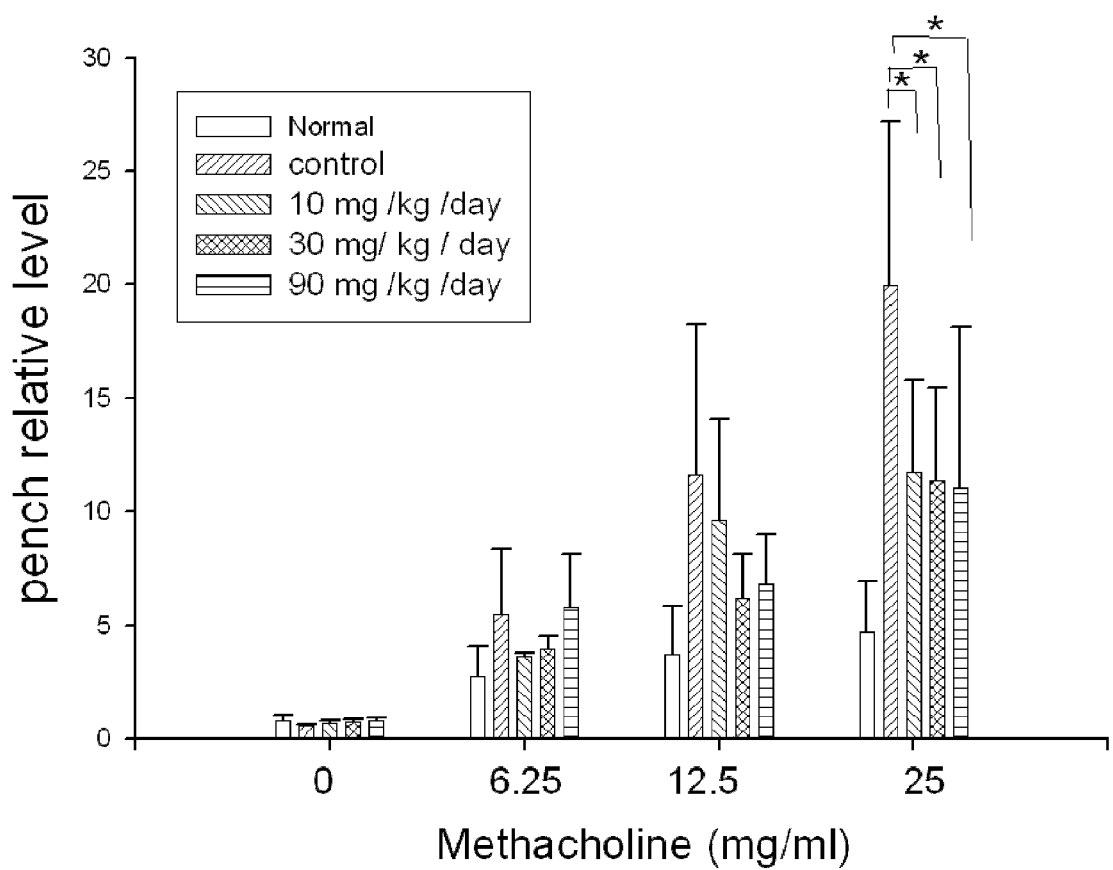
FIG. 1 is a diagram showing the effect of *Dendrobii Herba* on AHR test of the mice for Example 2, in terms of the pench relative level (Penh) as recorded and analyzed by Buxco XA system. The negative group (n=6, □) was healthy mice. The control group (n=10, ▨)was sensitized with OVA but without *Dendrobii Herba* treatment. The treatment groups sensitized with OVA were fed with a dose of 10 mg/kg/day (n=8, ⊠),30 mg/kg/day (n=8, ▧)and 90 mg/kg/day (n=8, ▤).The Penh were recorded and analyzed by Buxco XA system. * indicating $p<0.05$.

Described herein is use of *Dendrobii Herba* polysaccharides for treating an allergic disease. "Polysaccharides" are polymers each consisting of a number of monosaccharides joined by glycosidic bonds. A polysaccharide molecule includes more than 10 monosaccharides of any types, e.g., glucose, fructose, galactose, xylose, or ribose. It can have a linear or a branched structure.

The polysaccharides used to practice the method of this invention can be prepared from *Dendrobii Herba* via any conventional methods. One example follows. Stems of a *Dendrobium* plant (e.g., *Dendrobium loddigesii, Dendrobium fimbriatum* var. *oculatum, Dendrobium chrysanthum, Dendrobium candidum ex Lindl*, or *Dendrobium nobil*) are collected, dried, and soaked in an alcohol (e.g., methanol, ethanol, or a mixture thereof) for a suitable period of time (e.g., 1-12 hours). After removing the alcohol via, e.g., evaporation, the resultant *Dendrobium* stems are soaked in pure water or a suitable water-containing solvent for a sufficient period of time (e.g., 12-16 hours). The water-containing solvent can be an aqueous salt (e.g., NaCl or KCl) solution, or a mixture containing >70% (e.g., 80%, 90%, or 95%) by volume water and <30% by volume a water miscible solvent (e.g., methanol or ethanol). Insoluble substances are removed via centrifugation or filtration, resulting in a soluble fraction. This fraction is then mixed with an alcohol (e.g., 30-70% ethanol) to precipitate polysaccharides. Optionally, before being mixed with the alcohol, the water-soluble fraction is diluted in warm water and kept at 50-70° C. for 20-60 minutes. The precipitates are collected by, e.g., centrifugation, and preferably, dried, to obtained the polysaccharides to be used in the method of this invention.

The *Dendrobii Herba* polysaccharides described above can be mixed with a pharmaceutically acceptable carrier, and optionally with another therapeutically active agent, to form a pharmaceutical composition. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of the polysaccharide-containing pharmaceutical composition. Examples of other carriers include dextrine, silicon oxide, magnesium stearate, cellulose, sodium lauryl sulfate, D&C Yellow #10, microcrystalline cellulose, mannitol, glucose, defatted milk powder, polyvinylpyrrolidone, and starch, or a combination thereof This pharmaceutical composition can then be presented in a variety of forms, such as tablet, capsule, powder, gel, or liquid.

The pharmaceutical composition is administered to a subject via suitable routes, e.g., oral administration, once or multiple times per day or administered once every several days. A solid formulation for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microglycolate, and alginic acid. Tablet binders that can be used include acacia, methylcellulose, sodium carboxymethylcellulose, polyvinylpyrrolidone (Povidone3), hydroxypropyl methylcellulose, sucrose, starch, and ethylcellulose. Lubricants that can be used include magnesium stearates, stearic acid, silicone fluid, talc, waxes, oils, and colloidal silica.

This solid formulation can be designed such that the composition is released in the intestine. For example, the composition is confined in a solid sub-unit or a capsule compartment that have respectively a matrix or a wall or a closure comprising an enteric polymer which dissolves or disperses at the pH of the small or large intestine to release the drug substance in the intestine.

In another example, the polysaccharides described above is mixed with one or more edible carriers to form a food product (e.g., yogurt, milk, or soy milk), or a food supplement (e.g., a nutrient supply or an herbal product). Examples of an edible carrier include starch, cyclodextrin, maltodextrin, methylcellulose, carbonmethoxy cellulose, xanthan gum, and aqueous solutions thereof Such food products can be prepared by methods well known in the food industry. As used herein, the term "food" broadly refers to any kinds of liquid and solid/semi-solid materials that are used for nourishing humans and animals, for sustaining normal or accelerated growth, or for maintaining stamina or alertness.

The polysaccharides described herein can be used to treat allergic diseases, e.g., allergic diseases associated with an increased level of eosinophil, IgE, a chemokine, or a Th2 cytokine. It is well known that an allergen triggers a cascade of immune responses, including T cell differentiation to Th2 effector cells; release of Th2 cytokine (e.g., IL-4, IL-5, IL-6, and IL-13), production of IgE; and activation of neutrophils such as eosinophils or mast cells. The immune responses triggered by an allergen result in various allergic diseases, such as asthma, pollen allergy, allergic conjunctivitis, and atopic dermatitis.

Asthma is a chronic illness involving the respiratory system. The cardinal features in humans are airway inflammation, hypersecretion of highly viscous mucus, and bronchoconstriction. This airway narrowing causes symptoms such as wheezing, shortness of breath, chest tightness, and coughing. These features may be triggered by such things as exposure to an environmental stimulant (or allergen), cold air, warm air, moist air, or emotional stress. In addition, allergic sensitization is also defined by production of IgE against environmental antigens, recruitment of lymphocyte and eosinophil into the lungs and in serum, and inducing the production of Th2 cytokines or chemokines. Public attention in the developed world has recently focused on asthma because of its rapidly increasing prevalence, affecting up to one in four urban children. See Craig M. Lilly, *Journal of Allergy and Clinical Immunology*, Vol. 115, Issue 4, Supplement 1, April 2005, Pages S526-S531.

The same as asthma, allergic conjunctivitis and atopic dermatitis both result from hypersensitive to allergen, such as pollen; however, the inflamed region and symptoms are varied. Similarly, these allergic diseases are also related to excess of Th2 cytokines or chemokines, and proportion to the number of IgE level and eosinophils in the inflamed region.

The conjunctiva is a thin membrane that covers the eye. When an allergen irritates the conjunctiva, common symptoms that occur in the eye include: ocular itching, eye lid swelling, tearing, photophobia, watery discharge, and foreign body sensation. The allergen will trigger a typical allergic progress aforementioned. The study showed that patients limited certain activities such as going outdoors, reading, sleeping, and driving. Therefore, treating patients with allergic conjunctivitis can improve their everyday quality of life.

Atopy, or atopic syndrome, is an allergic hypersensitivity affecting parts of the body not in direct contact with the allergen. It may involve eczema (atopic dermatitis), allergic conjunctivitis, allergic rhinitis and asthma. There appears to be a strong hereditary component. Atopic syndrome can be fatal for those who experience serious allergic reactions such as anaphylaxis, brought on by reactions to food or environment. Although atopy has various definitions, most consistently it is defined by the presence of elevated levels of total and allergen-specific IgE in the serum of patient, leading to positive skin-prick tests to common allergens. Since the twentieth century, many mucosal inflammatory disorders have become dramatically more common; atopy is a classic example of such a disease. It now affects 10-20% of children and 1-3% of adults in industrialized countries, and its prevalence there has more than doubled in the past thirty years.

The *Dendrobii Herba* polysaccharides described herein can also be used to increase the population of T regulatory cells in the intestinal lamina propria site via, e.g., oral administration. The term "T regulatory cell" used herein refers to a specialized subpopulation of T cells that act to suppress activation of immune system and thereby maintain immune system homeostasis and tolerance to self antigens. Sometimes it also called suppressor T cells. T regulatory cells come in many flavors, including those that express the CD8 transmembrane glycoprotein (CD8+ T cells), those that express CD4, CD25 and Foxp3 (CD4+CD25+ regulatory T cells or "Tregs") and other T cell types that have suppressive function. In one embodiment, the T regulatory cells refer to the population which expressed CD4 and CD25.

The term "intestinal lamina propria" used herein refers to a thin layer of loose connective tissue which lies beneath the epithelium and together with the epithelium constitutes the mucosa. In this region, there are many immune cells retained here, for example, dendritic cells, macrophages, T cells, B cells or mast cells etc.

In another example, the polysaccharides also can be administrated to a subject to reduce the subject's IgE levels in serum and BALF. IgE plays a key role in the pathogenesis of allergy. Like other immunoglobulins, IgE is produced by B-lymphocytes following exposure of a foreign antigen from environment. When two or more molecules of IgE bound to the surface of a cell are simultaneously linked to its specific allergen, the cell will immediately release preformed inflammatory cytokines including histamine, which induce the immediate affects or early phase of allergy. These cytokines recruit eosinophils, macrophages and more basophils to the area. These newly synthesized substances and the cells they recruit are key players in the late phase of the allergic response. The close association between IgE, allergy, and asthma has long been recognized (Platts-Mills T A E, *Am J Respir Crit Care Med*, 164:S1-S5, 2001; Milgrom H, et al., *N Eng J Med.*, 341:1966-73, 1999). In one embodiment, mice fed with the polysaccharides extracted from *Dendrobii Herba* had lower level of IgE in serum and in BALF. Also these mice had fewer eosinophils and cytokines or chemokines which attracted the immune cells and stimulate airway epithelium. Therefore, the polysaccharides extracted from *Dendrobii Herba* could treat asthma.

In yet another example, the polysaccharides are used to reduce airway-remodeling resulted from inflammation by orally administrating the subject with polysaccharides extracted from *Dendrobii Herba*.

The term "airway remodeling" used herein refers to structural changes that occur in conjunction with, or because of, chronic airway inflammation. Airway remodeling results in alterations in the airway epithelium, lamina propria, and submucosa, leading to thickening of the airway wall. Consequences of airway remodeling in asthma include incompletely reversible airway narrowing, bronchial hyperresponsiveness, airway edema, and mucus hypersecretion.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Example 1

Preparation of Polysaccharides from *Dendrobii Herba*

2 kg of fresh *Dendrobii Herba* was dried to form the dry material, and then the dry material was immersed and treated with 20 L of methanol to obtain a treated plant. The treated plant was treated with a de-methanol process, and then immersed in water overnight to obtain an overnight water solution. The overnight water solution was extracted with 24 L warm water at the temperature ranged 60° C. for 30 min, and then centrifuged by the centrifuge (ER-RC13 C-124, HITACH) at 5,000 rpm and 10° C. After the centrifugation, the supernatant was filtered through 6 μm filter paper. The filtrate was precipitated with 50% (w/v) ethanol to obtain the polysaccharides.

Example 2

The Effect of Polysaccharides Extracted from *Dendrobii Herba* on Asthma

Set Up an Animal Model of Asthma

BALB/c male mice were randomly grouped into normal group (n=6, healthy mice as negative control), the control group (n=10, mice sensitized with OVA but without the treatment of the polysaccharides extracted from *Dendrobii Herba*), the treatment groups sensitized with OVA fed with a dose of 10 mg/kg/day (n=8), 30 mg/kg/day (n=8) and 90 mg/kg/day (n=8). Except the normal group, all the mice were immunized with an intraperitoneal injection of 20 and 50 μg/ml OVA (Sigma, USA) in phosphate-buffered saline (PBS) combined with the 2 mg and 5 mg $Al(OH)_3$ as adjuvant on Day 1 and 14, respectively. Negative control mice were given intraperitoneal injection of 1×PBS on each immunization. All mice were exposed to 1% OVA in PBS for 20 min by ultrasonic nebulizer (Buxco) on Day 28, 29, 30. On Day 31, all mice were subjected to AHR (Airway hyperresponsiveness) test by various concentration of methacholine, and sacrificed the next day (the method was referred to Charles Perkins et al., *J. Allergy Clin. Immunol.*, 118(2):410-419). On Day 0, 21 and after AHR test, bloods of the mice were collected from the retro-orbital venous plexus. The blood samples were tested for OVA-specific antibodies.

Determination of Airway Hyperresponsiveness to Methacholine

Mice were placed, unrestrained, in cylindrical plexiglass plethysmograph chambers that were connected to a Buxco nebulized control aerosol delivery system and a Buxco Max II apparatus for analyzing barometric plethysmography (Buxco Electronics, Sharon, Conn.). Baseline measurements of enhanced pause (Penh) were made over a 5-minute period. Penh, referring to a unit-less measure of airflow obstruction, reflects changes in pulmonary function related to quantitative differences in time and extent between inspiration and expiration. Specifically, Penh is considered a parameter that reflects changes in waveform of the measured box pressure signal that are a consequence of bronchoconstriction and is an index of airway obstruction. The severity of asthma can be evaluated by the level of Penh (Zhang et al., *J. Allergy Clin. Immunol.*, February; 113(2):320-6, 2007).

Mice were then challenged for 3 minutes by means of inhalation of aerosolized, β-methacholine in PBS produced with a nebulizer (Buxco Electronics, Sharon, Conn.), starting at a methacholine concentration of 6.25 mg/mL. Penh measurements were starting 3 minutes after completion of exposure to the aerosolized methacholine, and average Penh values for the 3-minute period were calculated. Subsequently, the procedure was then serially repeated and the concentration of methacholine was changed to 12.5 mg/mL and 25 mg/mL. All the recorded data were normalized to the baseline measurements, and the results of each group were showing in FIG. 1.

AHR contributes significantly to airway obstruction and the cardinal symptoms in asthma, such as breathlessness, chest tightness, coughing and difficultly speaking. Accordingly, inhibition of AHR can ease the severity of asthma. As shown in FIG. 1, all of the three treatment groups exhibited significantly decreased Penh responses to aerosolized 25 mg/mL methacholine compared to the control group. It was indicated that the polysaccharides extracted from *Dendrobii Herba* could inhibit AHR, therefore it could treat asthma.

Brochoalveolar Lavage Fluid (BALF) Analysis

"Brocho-alveolar lavage fluid" is the fluid obtained by washout of the alveolar compartment of the lung. It is used to determine biochemical and inflammatory changes in the interstitial lung tissue, thereby assessing the efficacy of the method of this invention.

After cervical dislocation, the trachea were exposed and incubated with a polyethylene catheter. BALF was collected from the mice by lavaging with 1 mL of PBS through the trachea. After the wash was centrifuged, the supernatant was used for antibody detection and a total cell count was obtained from the pellet. Cytospin slides were prepared and stained by Liu's staining, a modification of Giemsa staining (Sevens, M. L. *Fundamentals of clinical hematology.*, W.B. Saunders company, 1997).

The cells of BALF from the mice were first stained by addition of 0.5 mL Liu's A solution (prepared by dissolving 0.18 g Eosin Y and 0.05 g Methylene blue in 100 mL methanol, followed by filtering the resultant solution through a No. 3 filter paper) for 30 seconds. Thereafter, 1 mL Liu's B solution (prepared by dissolving 0.12 g Methylene blue, 0.14 g Azure B, 2.52 g $Na_2HPO_4$ and 1.26 g $KH_2PO_4$ in 100 mL $H_2O$, followed by filtering the resultant solution through a No. 3 filter paper) was added to mix with the Liu's A stain immediately. After a reaction time of 60 seconds, the slide was washed with water to clean out the stain solution. The slide were air-dried and then examined under an optical phase microscope, and the differentials were obtained after counting 300 cells. The results were showed in FIG. 2 and FIG. 3.

Figure 2:
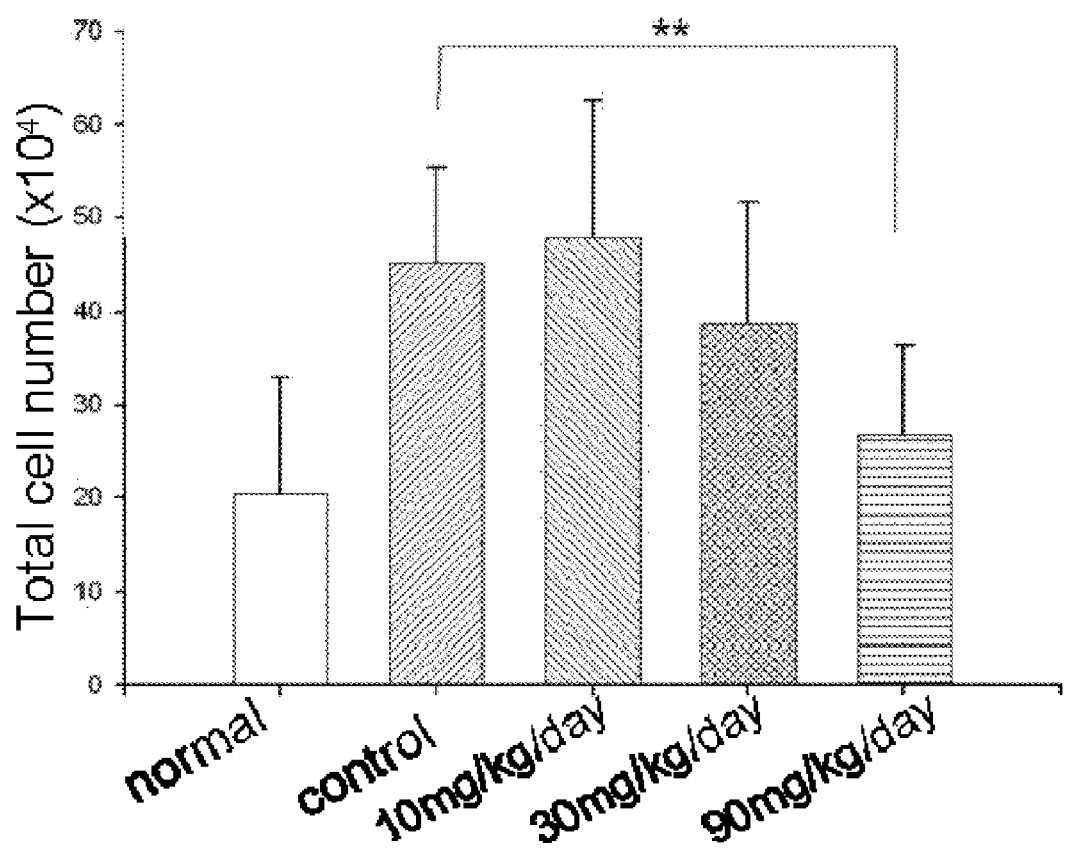
FIG. 2 is a diagram showing the total cell numbers counted in BALF from the mice in Example 2. The negative group (n=6, □) was healthy mice. The control group (n=10, ▨)was sensitized with OVA but without *Dendrobii Herba* treatment. The treatment groups sensitized with OVA were fed with a dose of 10 mg/kg/day (n=8, ⊠),30 mg/kg/day (n=8, ▧)and 90 mg/kg/day (n=8, ▤).* indicating $p<0.05$.
Figure 3A:
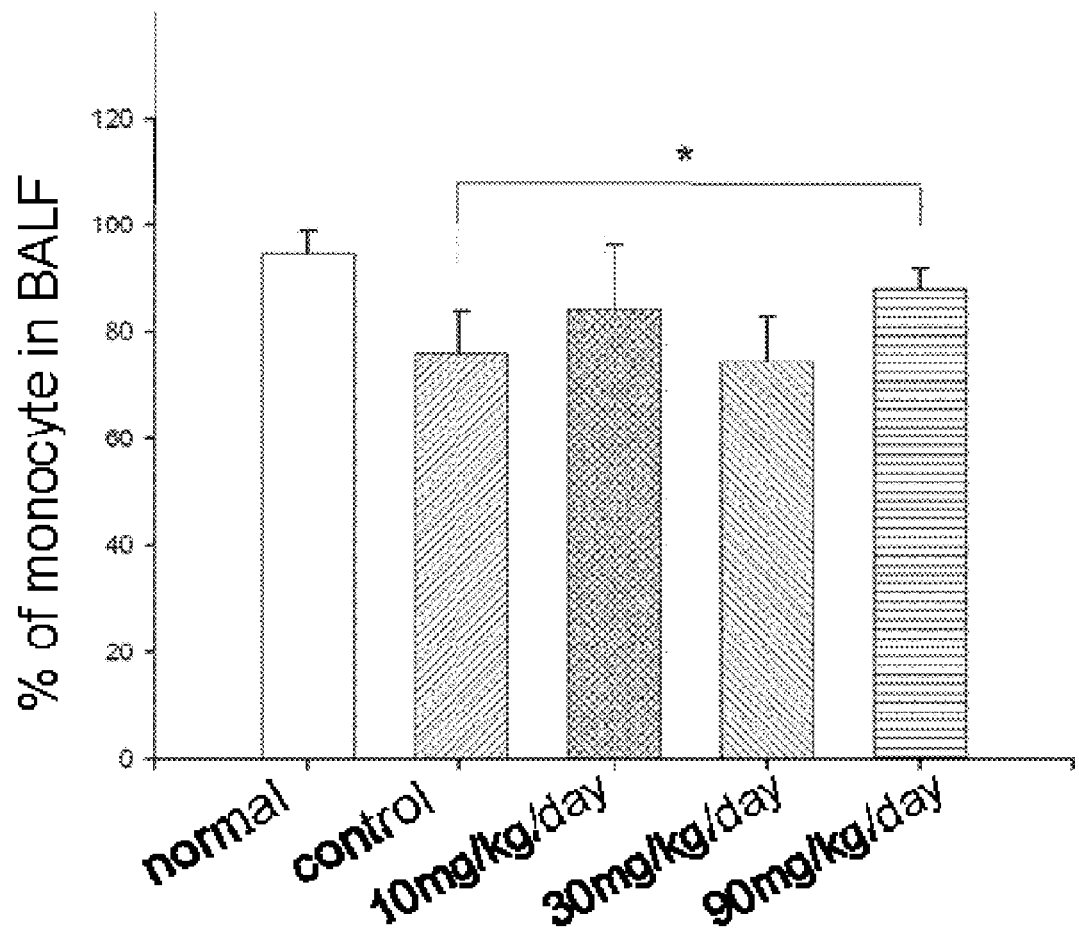
FIG. 3 is a diagram showing the percentage of leukocytes in BALF from the mice in Example 2. Part A to C represents the result of the percentage of the monocyte, lymphocyte and eosinophil, respectively in BALF. The negative group (n=6, □) was healthy mice. The control group (n=10, ▨)was sensitized with OVA but without *Dendrobii Herba* treatment. The treatment groups sensitized with OVA were fed with a dose of 10 mg/kg/day (n=8, ⊠),30 mg/kg/day (n=8, ▧)and 90 mg/kg/day (n=8, ▤).* indicating $p<0.05$.
Figure 3B:
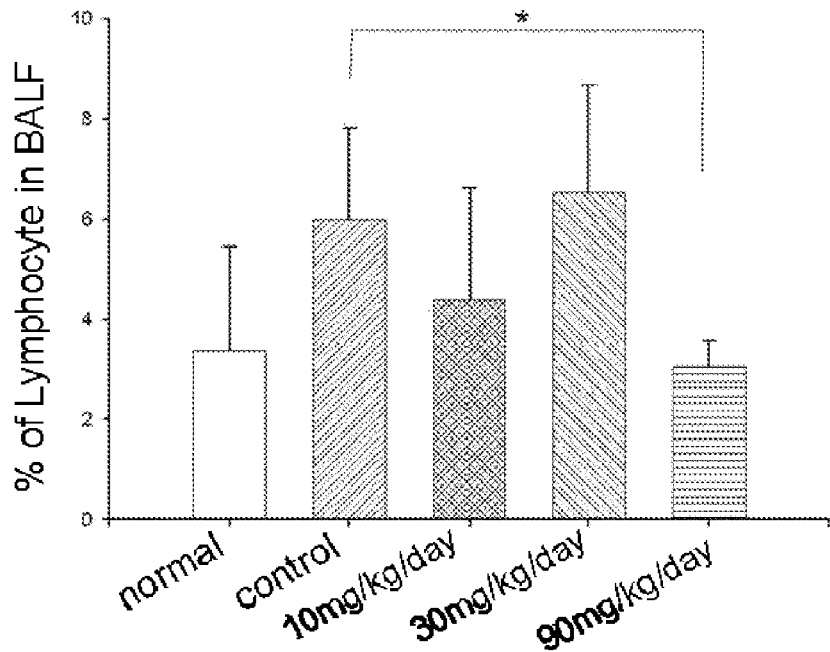
Figure 3C:
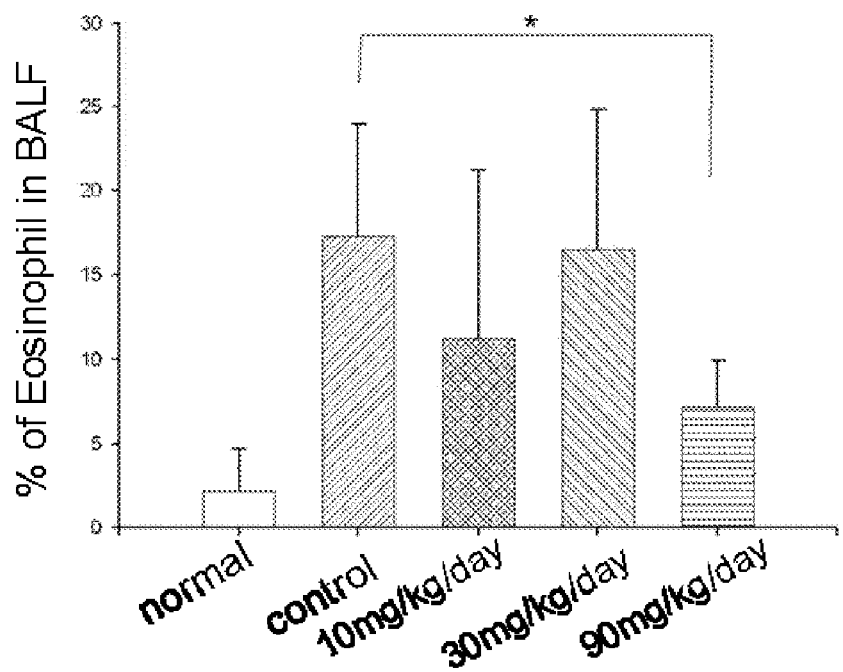

As shown in FIG. 2, the number of total cells in 90 mg/kg/day group compared to the control group had significant decreased. Furthermore, the percentages of each cell type (eosinophils, neutrophils, monocytes and lymphocytes) are shown in FIG. 3. Eosinophil and lymphocyte percentages were significant reduced in the group orally treated with 90 mg/kg/day *Dendrobii Herba* polysaccharides compared to the control group.

Without being bound by theory, the polysaccharides obtained from *Dendrobii Herba* may be effective in treating asthma through the following mechanism. It has been reported that eosinophils play the key role in asthma development. See Walsh G. M., *Curr Opin Hematol.*, 8(1):28-33, 2001; and Menzies-Gow A et al., *J Asthma.*, 38(8):605-13, 2001. As shown above, the Dendrobium polysaccharides reduced numbers of eosinophils in the BALF, thereby alleviating asthmatic symptoms.

Effect of the Polysaccharides Extracted From *Dendrobii Herba* on Eosinophilia and Airway Remodeling in Lungs After BALF was obtained, the lung tissue was fixed in 10% neutral buffered formalin for 24 h. The lung tissue was embedded in paraffin, and then cut into 5 μm thickness sections. The slices were stained with H&E solution (hematoxylin; Sigma MHS-16 and eosin, sigma HT110-1-32). The results were photographed and showed in FIG. 4.

Asthma is characterized by a specific pattern of inflammation in the airway mucosa, and involves the infiltration of eosinophils, increased number of $T_H2$ cells relative to $T_H1$ cells. In addition, there are characteristic structure changes to the airway, termed remodeling, some of which might even precede the development of the disease. These structural changes seen in asthmatic patients can include thickening of the airway wall reticular basement membrane, formation of an abnormal elastic fiber network, alterations in airway cartilage structure, angiogenesis, and increase in airway smooth muscle mass.

In the present invention, control group obviously displayed the thickening of the airway epithelium basement and the narrowness in bronchial tubes. As the dose of *Dendrobii Herba* polysaccharides treatment went up, so the features of airway remodeling reduced and the diameter of bronchial tubes came to nature. Combination with the results in FIG. 2, the present invention features a method to decrease the number of eosinophil and lymphocyte, also relief the symptom of airway remodeling.

Oral Treatment of the Polysaccharides Extracted From *Dendrobii Herba* Can Increase the Percentage of Treg in Intestinal Lamina Propria Mice were killed by cervical dislocation. The small intestine was immediately removed, and flushed in HBSS (with HEPES, $Ca^{2+}$ and $Mg^{2+}$-free). Peyer's patchs were carefully dissected out and cut into segments. To remove the epithelium cells, the segments were shaken with 1 mM dithiothreitol solution (DTT, Amresco, USA) and 1 mM ethylenediaminetetraacetic acid (EDTA, Sigma, USA) at 37° C. for one hour. After the incubation, the segments were minced into 1-mm pieces and digested in RPMI 1640 (Gaithersburg, USA) contained with 30 unit/mL Collagenase Type I (Sigma, USA) and 10 unit/mL Collagenase Type II (Sigma, USA) as well as 10% fetal calf serum at 37° C. for one hour. The digested tissue were passed through a nylon mesh (Small Parts, USA) to obtain the cells. After thorough washing, the mononuclear cells were obtained by the centrifugation on Percoll.

Figure 5:
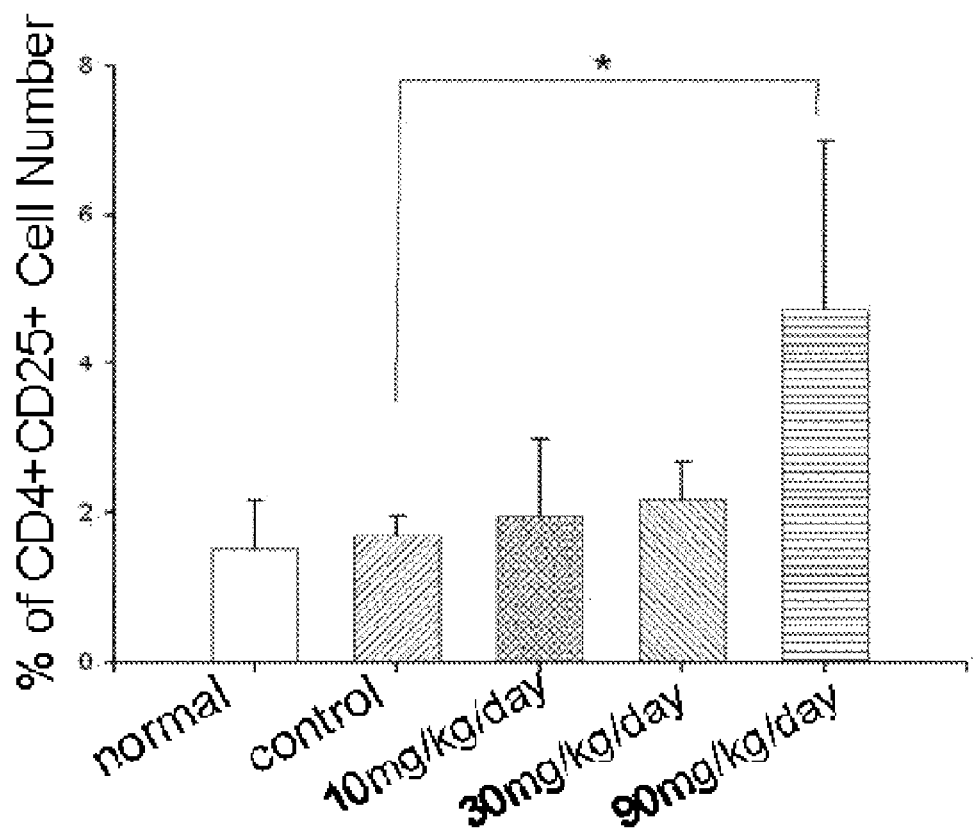
FIG. 5 is a diagram showing the percentage of T regulatory cells in the intestinal lamina propria lymphocytes from the mice in Example 2. The ratios of CD4+CD25+ cells were analyzed by Flow cytometry. The negative group (n=6, □) was healthy mice. The control group (n=10, ▨)was sensitized with OVA but without *Dendrobii Herba* treatment. The treatment groups sensitized with OVA were fed with a dose of 10 mg/kg/day (n=8, ⊠),30 mg/kg/day (n=8, ▧)and 90 mg/kg/day (n=8, ▤).* indicating $p<0.05$.

The mononuclear cells were adjusted to $1 \times 10^6$ cells/mL, and added to the tube to incubated with FITC conjugated CD4 antibody (BD Biosciences, USA) and PE conjugated CD25 antibody (BD Biosciences, USA) for 30 min at 4° C. in the dark. The samples were washed twice in cold PBS and analyzed by two-color cytometry performed with a FACScan (Becton Dickinson Bioscience, USA). The number of CD4+ CD25+ cells divided by the number of CD4+ cell was the percentage of Treg. The results were shown in FIG. 5. Mice fed with 90 mg/kg/day *Dendrobii Herba* polysaccharides had more Treg in the intestinal lamina propria.

Figure 6A:
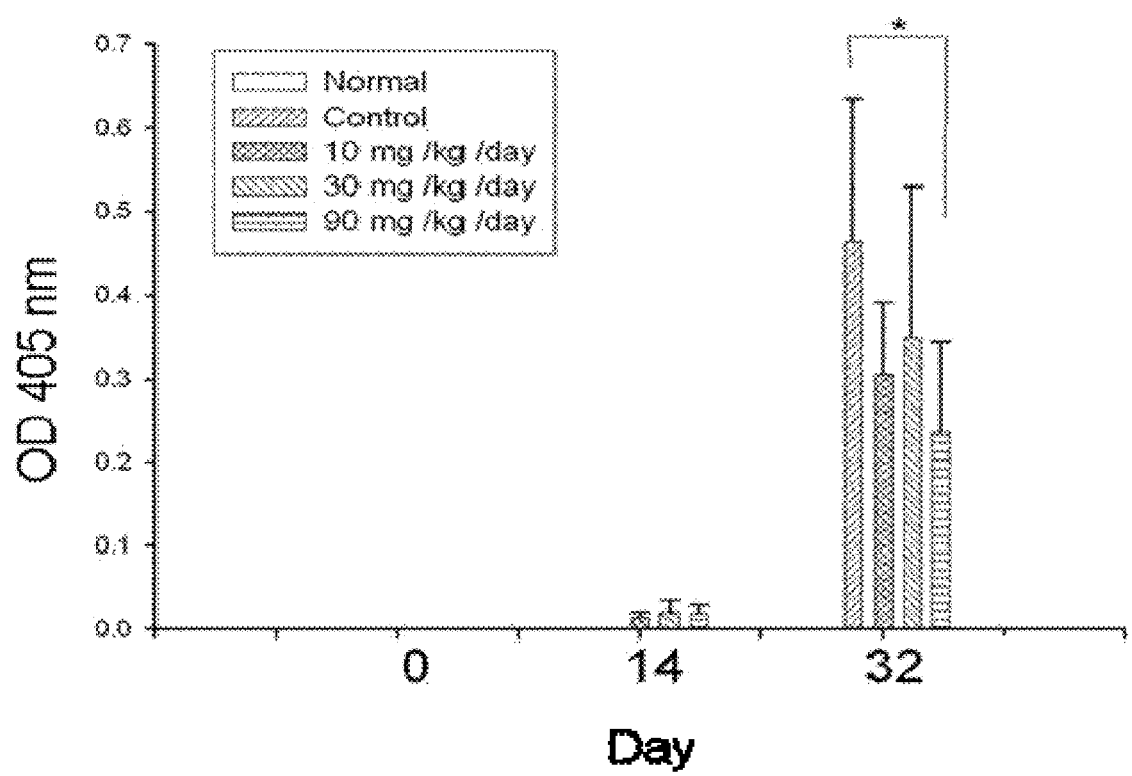
FIG. 6 is a diagram showing the effects of *Dendrobii Herba* on the levels of OVA-specific IgE from the mice in Example 2. Part A represents the result of serum level, and part B represents the result of BALF level. The negative group (n=6, □) was healthy mice. The control group (n=10, ▨)was sensitized with OVA but without *Dendrobii Herba* treatment. The treatment groups sensitized with OVA were fed with a dose of 10 mg/kg/day (n=8, ⊠)30 mg/kg/day (n=8, ▨)and 90 mg/kg/day (n=8, ▤).** indication p<0.01.
Figure 6B:
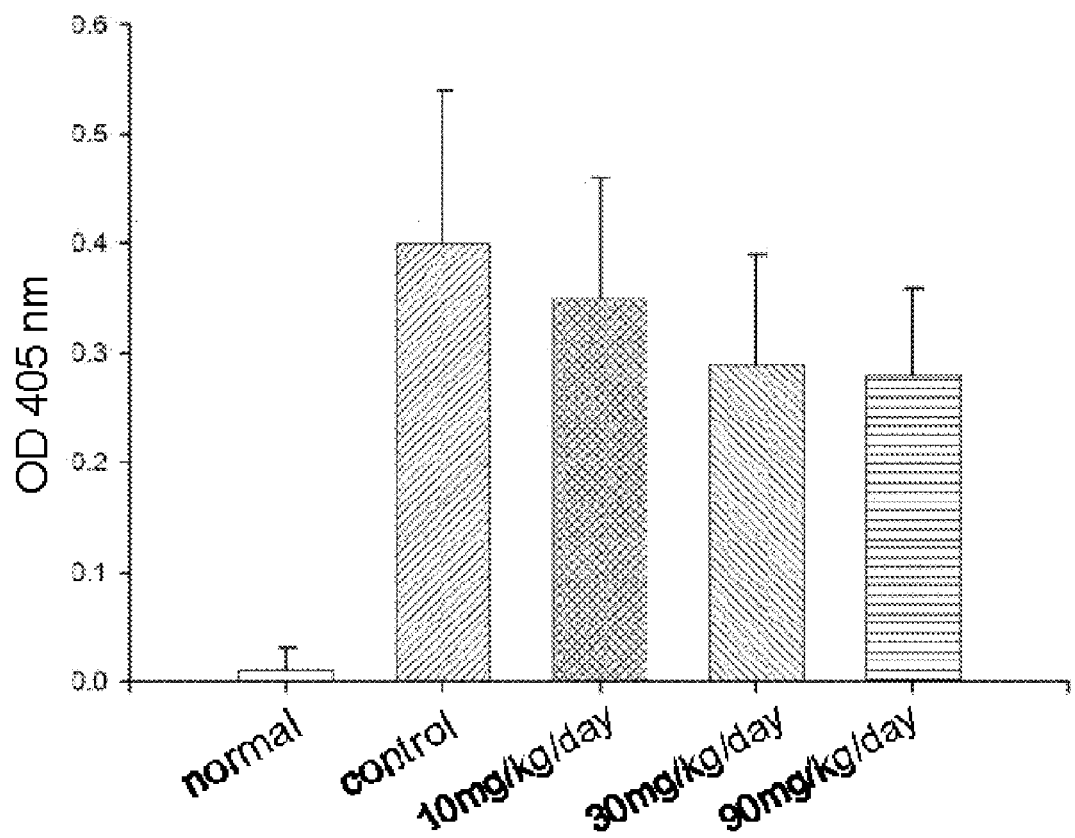
Figure 7A:
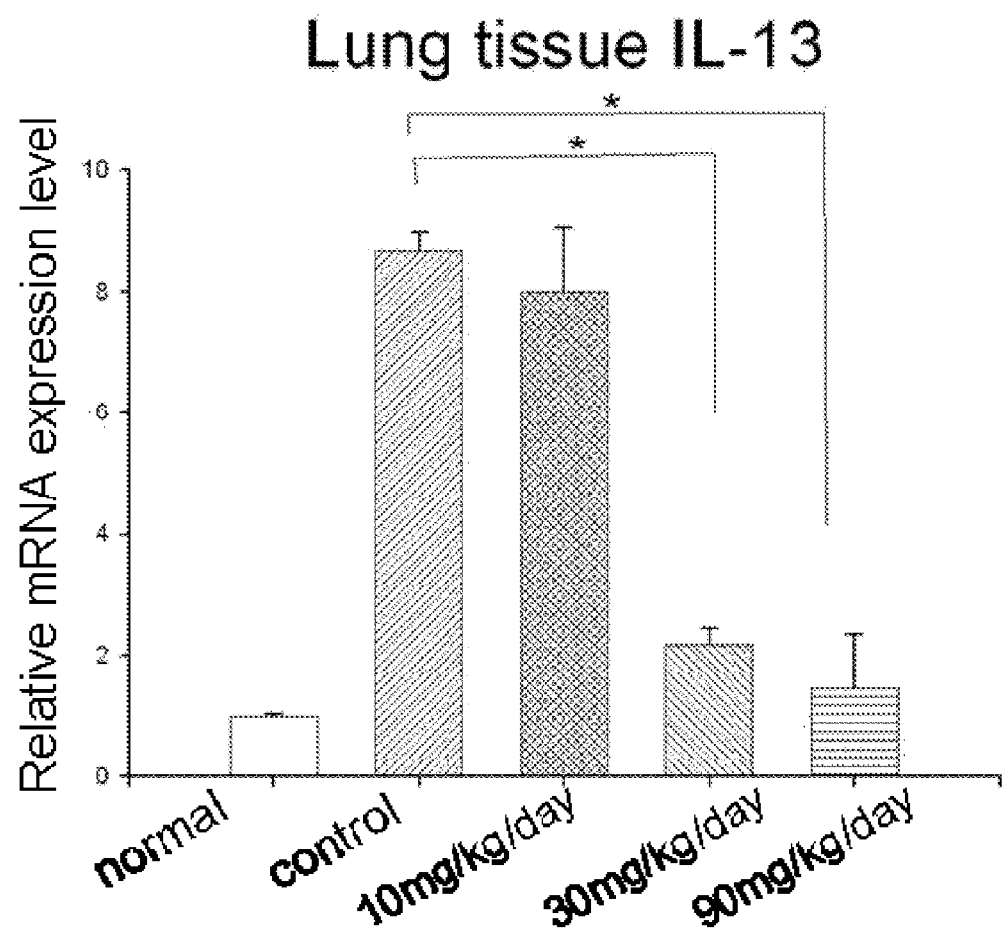
FIG. 7 is a diagram showing the RT-PCR results of whole lung tissue of the mice in Example 2. Part A to E represent the results of the gene expression level of IL-13, eotaxin-1,3-dioxygenase (IDO), IL-17, and Thymic stromal lymphopoietin (TSLP), respectively. All of the mRNA expression level is normalized to β-actin mRNA. The negative group (n=6, □) was healthy mice. The control group (n=10, ▨)was sensitized with OVA but without *Dendrobii Herba* treatment. The treatment groups sensitized with OVA were fed with a dose of 10 mg/kg/day (n=8, ⊠)30 mg/kg/day (n=8, ▨)and 90 mg/kg/day (n=8, ▤).* indicating p<0.05.
Figure 7B:
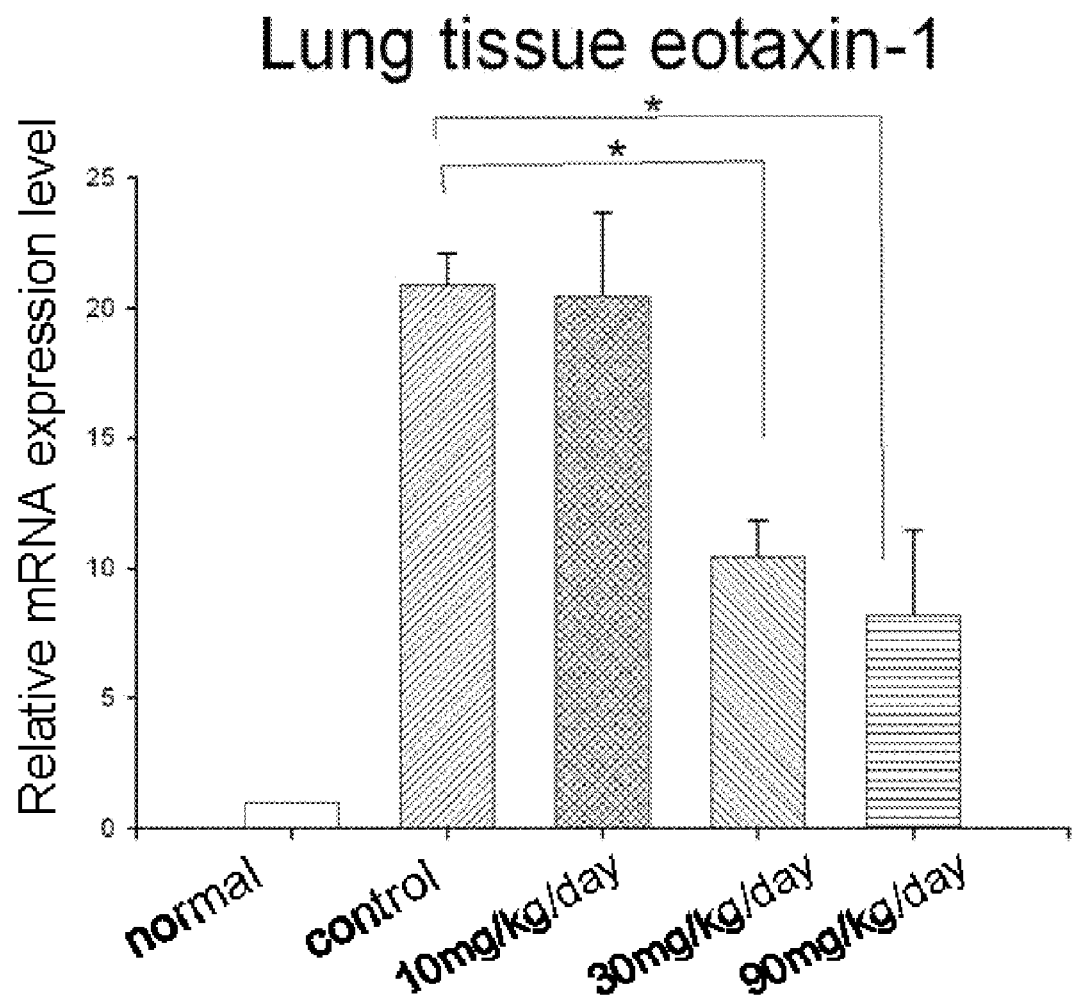
Figure 7C:
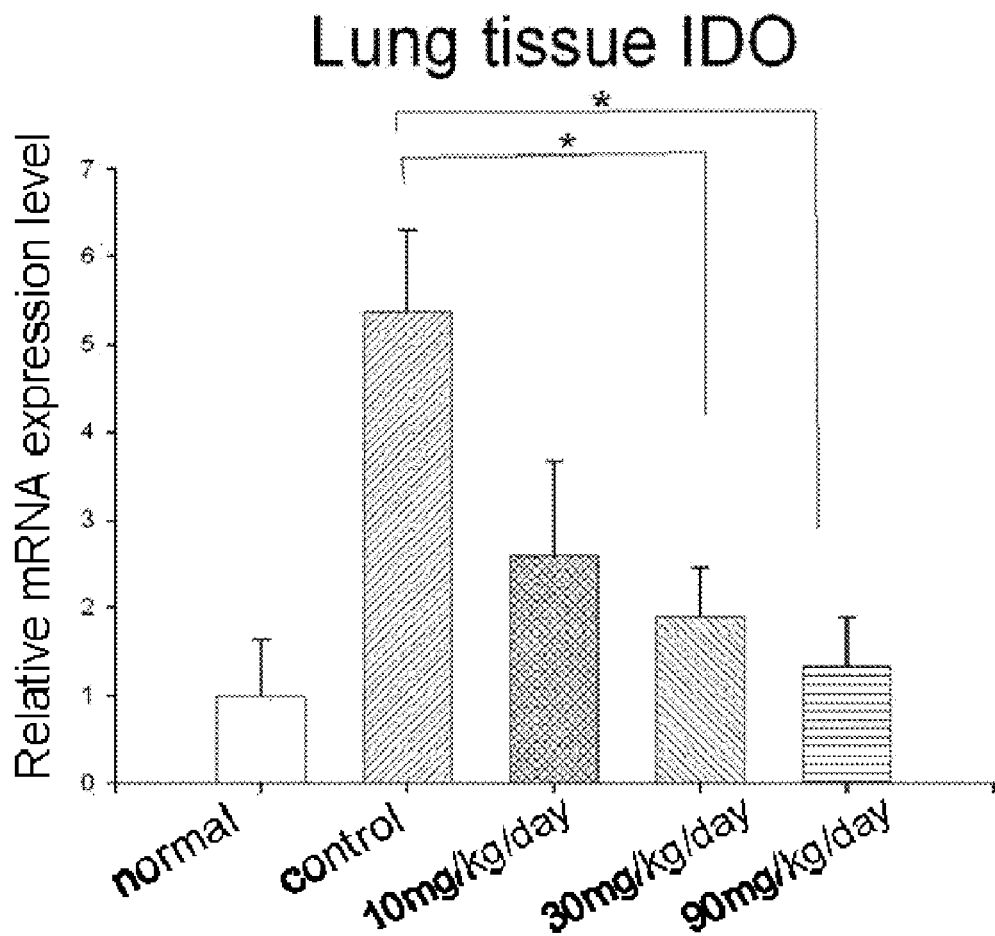
Figure 7D:
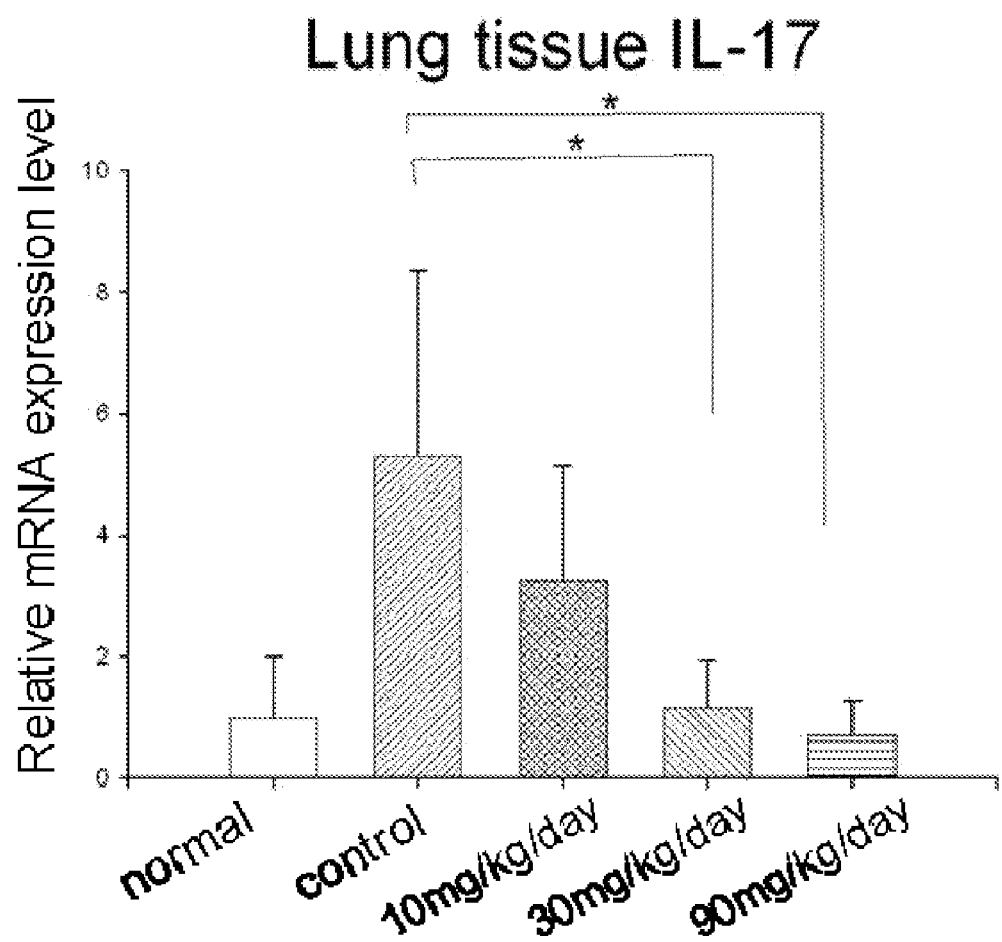
Figure 7E:
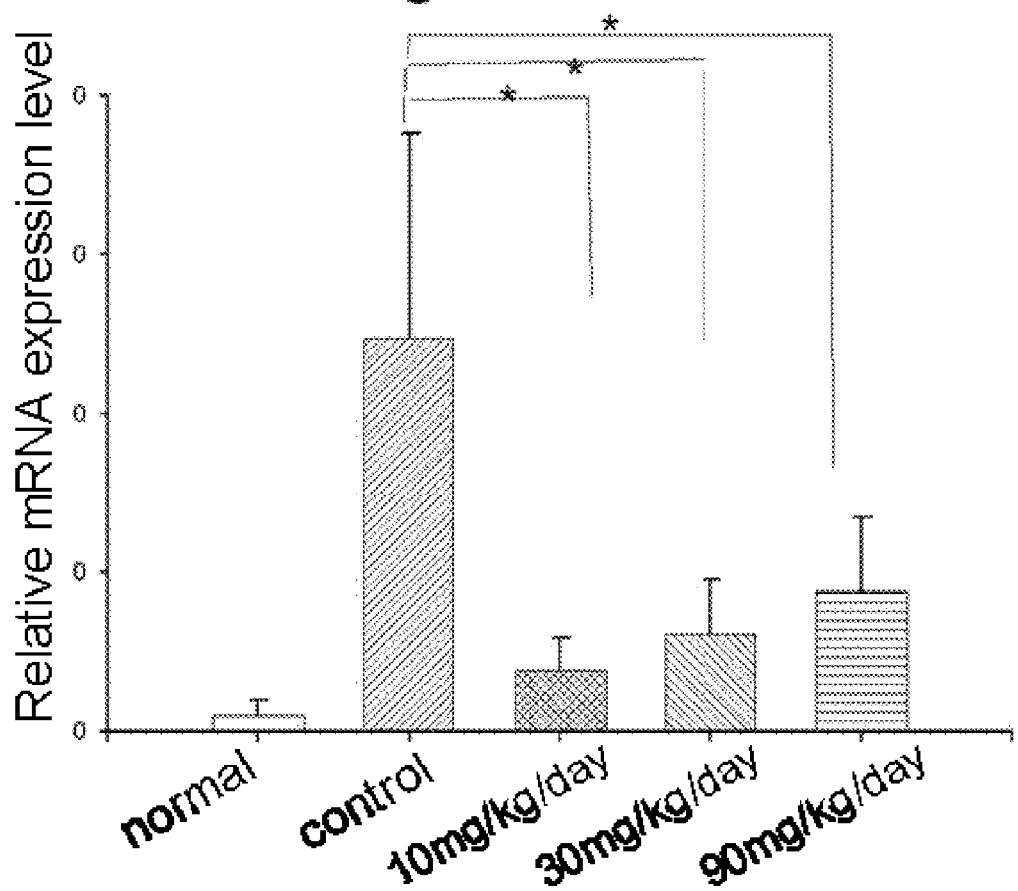

Effects of the Polysaccharides Extracted From *Dendrobii Herba* on the Serum and BALF Levels of OVA-specific IgE in the Mice Sensitized With OVA The serum collected on Day 1, 14 and the day before sacrificed and BALF were used to detect the OVA-specific IgE by ELISA. The assay was performed according to the manufacture's direction. Serum samples in duplicate were diluted to 1:50 and BALF was not diluted. The antibody used here was AP conjugated goat-anti-mouse IgE bought from Southern BioTech (USA). As shown in FIG. 6, serum IgE significant decreased in 90 mg/kg/day *Dendrobii Herba* polysaccharides group. However, the IgE level of BALF was also on the downward trend in the same group.

Nowadays, many researches have indicated that IgE is the key molecules in immediate allergic reactions, because it can form a bridge between allergens and neutrophils and triggers cellular degranulation, with liberation of countless preformed mediators and cytokines (Holgate S et al., *J Allergy Clin. Immunol.*, 115:459-465, 2005; Cooper P J, *Parasite Immunol.* 26:455-467, 2004; Milgrom H, et al., ut supra). Therefore, neutralization or inhibition of IgE synthesis could be a rational option for the treatment of allergic diseases (Sarinho E and Cruz A A, *J Pediatr (Rio J)*, 82(5 Suppl):S127-32, 2006; Wagelie-Steffen A L et al., *Clin Chest Med.*, 27:133-147, 2006; Clark J et al., *J Asthma*, 43:87-93, 2006). In the present invention, 90 mg/kg/day *Dendrobii Herba* polysaccharides could decrease the level of IgE in serum and in lungs of mice with asthma. In view of these data, *Dendrobii Herba* polysaccharides have great potential to treat allergic disease or asthma.

Effects of the Polysaccharides Extracted From *Dendrobii Herba* on the Gene Expression in Lung Tissue From the Mice Sensitized with OVA The tissue was excision and cut into pieces. Total RNA was then isolated with rare RNA total RNA isolation reagent (Gsharp Corporation, Taiwan) according to the manufacture's direction. Reverse transcription used 5 μg RNA for cDNA synthesis with MMLV reverse transcrptase (Promega, USA) in a total volume of 40 μl. The portion of the resulting reverse-transcription product (1 μl) was used to PCR amplification. The primer sequences used for IL-13, eotaxin-1, IDO, IL-17, and TSLP were listed as following:

| Gene | | sequence | length |
|---|---|---|---|
| β-actin | Forward | 5'-GTGGGCCGCCCTAGGCACCA-3'<br>(SEQ ID NO:1) | 241 bp |
| | Reverse | 5'-TGGCCTTAGGGTTCAGGGGG-3'<br>(SEQ ID NO:2) | |
| IL-13 | Forward | 5'-GGAGCTGAGCAACATGACACA-3'<br>(SEQ ID NO:3) | 142 bp |
| | Reverse | 5'-GGTCCTGTAGATGGCATTGCA-3'<br>(SEQ ID NO:4) | |

-continued

| Gene | | sequence | length |
|---|---|---|---|
| eotaxin-1 | Forward | 5'-GGGCAGTAACTTCCATCTGTCTCC-3' (SEQ ID NO:5) | 267 bp |
| | Reverse | 5'-CACTTCTTCTTGGGGTCAGC-3' (SEQ ID NO:6) | |
| IDO | Forward | 5'-TTATGCAGACTGTGTCCTGGCAACTG-3' (SEQ ID NO:7) | 340 bp |
| | Reverse | 5'-TTTCCAGCCAGACAGATATATGCGGAG-3' (SEQ ID NO:8) | |
| IL-17 | Forward | 5'-GCTCCAGAAGGCCCTCAGA-3' (SEQ ID NO:9) | 142 bp |
| | Reverse | 5'-AGCTTTCCCTCCGCATTGA-3' (SEQ ID NO:10) | |
| TSLP | Forward | 5'-TGCAAGTACTAGTACGGATGGGGC-3' (SEQ ID NO:11) | 323 bp |
| | Reverse | 5'-GGACTTCTTGTGCCATTTCCTGAG-3' (SEQ ID NO:12) | |

PCR conditions to amplify these genes were 95° C. for 5 min for initial degeneration and followed by 94° C. for 30 sec, 58° C. for 30 sec and 72° C. for 1 min. All of the gene expression level was normalized with β-actin mRNA. As shown in FIG. 7, the expression level of mRNA of cytokine or chemokine in lungs were lower in the group fed with 30 mg/kg/day and 90 mg/kg/day polysaccharides extracted from *Dendrobii Herba*.

Selective recruitment of eosinophils by some chemokines, such as IL-13, eotaxin-1, IL-17 and TSLP, into the airways during allergic inflammation suggests that eosinophil-specific chemoattractant are produced and released throughout the course of pulmonary inflammation (Rothenberg M E., *N. Engl. J. Med.*, 338:1592-1600, 1998; Lacy P et al., *Chem. Immunol.*, 76:134-155, 1998). Furthermore, it is acknowledged that an increase of IDO, which was induced by eosinophils, will lead to the apoptosis of Th1 and promote Th2 polarization. In the result, eosinophil may maintain Th1-Th2 imbalance seen in allergic asthma through expression functionally active IDO in lymphoid tissue (Odemuyiwa S O et al, *J Immunol. Nov.* 15, 2004; 173(10):5909-13). Therefore, inhibition of these protein of production is helpful to block the progression of asthma. In the present invention, mice with oral treatment of the polysaccharides from *Dendrobii Herba* had lower gene expression level mentioned above, which were related to recruit eosinophils or lymphocytes. Because these two cells played the major role in the process of allergic disease, especially asthma, reduced the chemokine could prevent the infiltration in the lungs. Consequently, the symptoms of allergic disease associated to eosinophil, such as asthma can be treated.

Example 3

The Effect of Polysaccharides Extracted from *Dendrobii Herba* on Pollen Allergy Extraction of Active Protein in Ragweed Pollen Ragweed pollen was purchased from Polyscience, Inc. (Polyscience, Inc., Warrington, Pa., U.S.A). Ragweed pollen (1 g) was treated with 500 μl ether and 20 ml 0.125 M ammonium bicarbonate for 48 hours at room temperature to obtain a first supernatant by centrifuging at 10000×g for 30 min. The treated pollen was treated with 12 ml 0.125M ammonium bicarbonate for 24 hours at room temperature to obtain a second supernatant by centrifuging at 10000×g for 30 min. The first and second supernatants were collected into a dialytic bag with the pore size of 3500 Da and dialyzed against 5 mM ammonium bicarbonate for 4 hours, then changed new 5 mM ammonium bicarbonate and continuously dialyzed for 24 hours. The final sample were lyophilized and stored at −20° C. until used. The ratio of extraction from pollen was 21.1%, and the extracts contained 11.9% of proteins.

Induction of Eye Conjunctivitis by Active Immunization and Treatment with Polysaccharides Extracted from *Dendrobii Herba*

The method of induction of eye conjunctivitis was modified by prior research (Schopf, L., et al., *Invest Ophthalmol Vis Sci*, 2005. 46(8): p. 2772-80). All Balb/c female mice of 8 weeks old were received a surgery of ovariectomy 11 days before the sensitization. Mice were injected intraperitoneally on Day 0, 7, 14 and 29 with 200 μg pollen extracts (contained 50 μg protein) and 4 mg Al(OH)$_3$ which dissolved in 200 μl PBS. On Day 8 and 15, mice were received an eye drops sensitization of 5 μl PBS containing 500 μg pollen extracts and 25 μg Al(OH)$_3$ on left eye. On Day 22, 23, 24 and Day 36, 37, 38, 39, 40, the mice were challenged with pollen extracts in PBS (1 mg in 3 μg PBS per eye) on left eye. Fifteen minutes after the challenge, the mice was received a measurement of tears, and observed lid swelling and conjunctiva redness. Normal mice were not received aforementioned sensitization but the same challenge. Control mice were received sensitization and challenge but no polysaccharides treatment. Some of the mice were orally administrated with 30 mg/kg/day or 90 mg/kg/day of polysaccharides extracted from *Dendrobii Herba* on Day 8 until sacrificed on Day 52.

Appearance Observation and Measurement of Tears

Allergic conjunctivitis is a hypersensitivity to allergy, for example, pollen. The symptoms consist of eyes that itch, lid swelling, excessive production of tears and redness of conjunctiva, or white portion of the eyes. To evaluate the efficacy of the treatment of polysaccharides, fifteen minutes after each challenge, the left eye of the mice were photographed and received a test for measuring tear production. In respect to tear production, a filter paper strip was used. The filter paper strip used herein was first immersed by 0.5 g phenol red (Sigma, USA), which was dissolved in 17.5 ml, 70% ethanol, and dried at room temperature overnight. The size of the filter paper strip was 1 mm wide and 20 mm long. It was placed at the junction of the middle and lateral thirds of the lower eye lid, after gently removing excess secretion from the lower eye lid. The standard time used to measure tear production in mice was 1 minute. The photographs of inflamed eye were shown in FIGS. 8A-8D, and the length of color change was shown in FIG. 9.

Figure 8A:
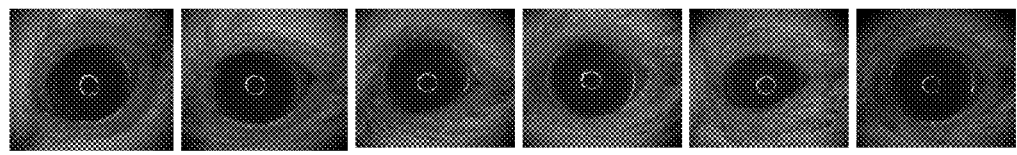
FIG. 8A is a photograph showing the inflamed eyes of the normal mice without sensitization 24 hours after challenge.
Figure 8B:
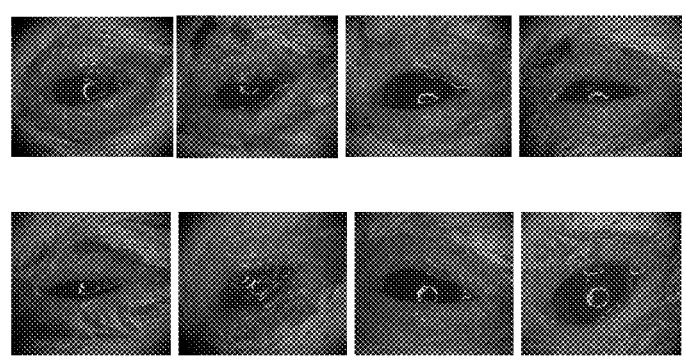
FIG. 8B is a photograph showing the inflamed eyes of the control mice which is active immunized but no treatment of polysaccharides 24 hours after challenge.
Figure 8C:
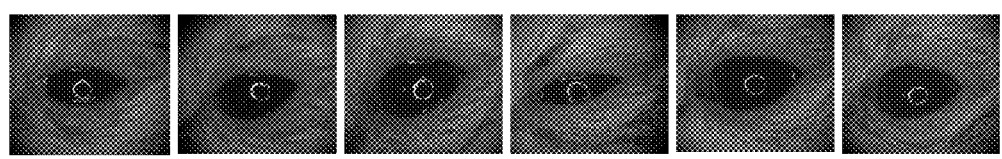
FIG. 8C is a photograph showing the inflamed eyes of the active immunized mice which are orally administrated with 30 mg/kg/day of polysaccharides extracted from *Dendrobii Herba*.
Figure 8D:
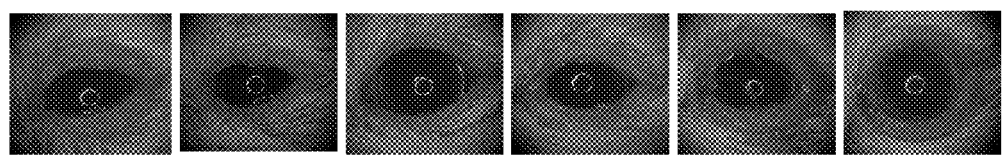
FIG. 8D is a photograph showing the inflamed eyes of the active immunized mice which are orally administrated with 90 mg/kg/day of polysaccharides extracted from *Dendrobii Herba*.

As the result shown in FIG. 8A, the eyes of normal mice were only slight redness and swelling, but those of control mice were serious swelling and inflamed (FIG. 8B). The mice orally administrated with 30 mg/kg/day (FIG. 8C) or 90 mg/kg/day (FIG. 8D) of polysaccharides extracted from *Dendrobii Herba* also had inflamed eyes; however, the symptoms of redness and swelling were relieved.

Figure 9:
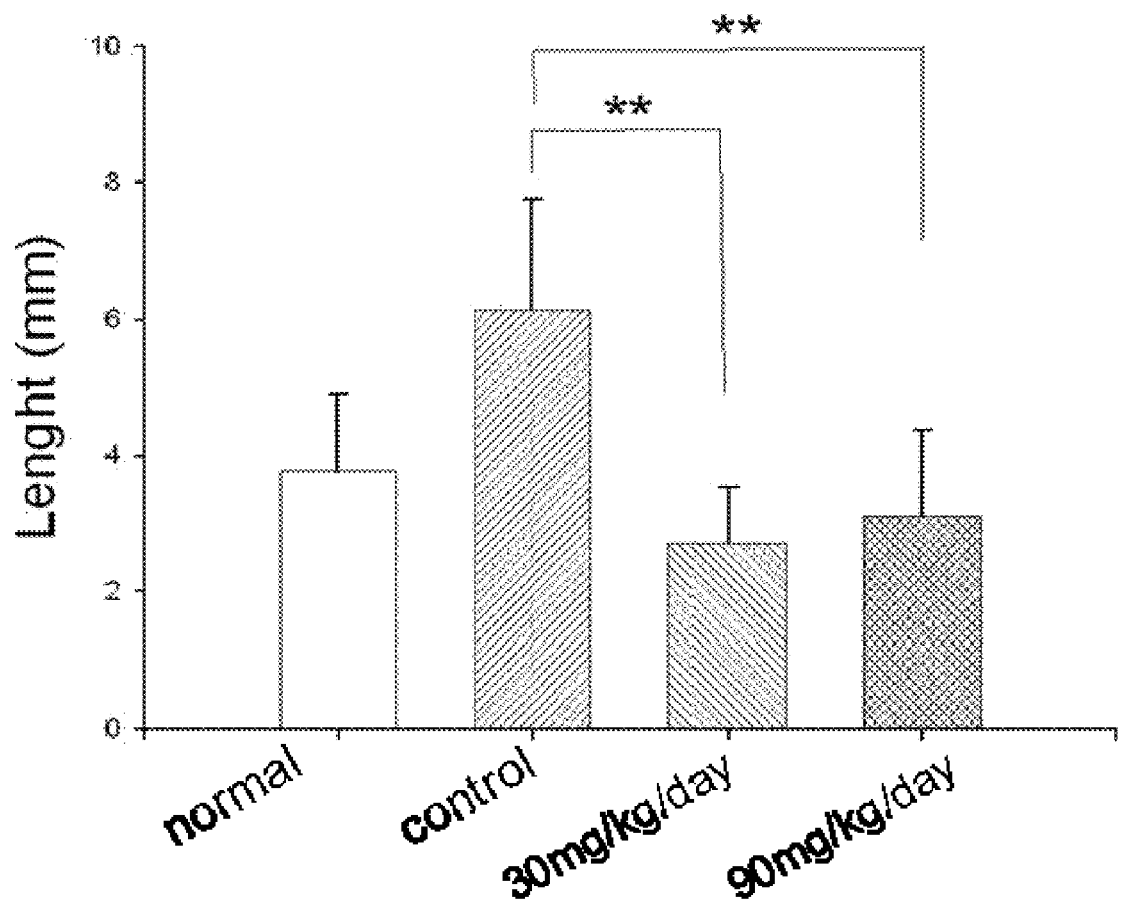
FIG. 9 is a diagram showing tear production in each group of mice by measuring the length of color change (mm) on filter paper script. ** indicating p<0.01.

As the result shown in FIG. 9, in accordance with the symptom of allergic conjunctivitis, the mice of control group produced more tears after contacting the pollen. The mice of orally administrated with 30 mg/kg/day or 90 mg/kg/day of polysaccharides extracted from *Dendrobii Herba* had significantly less tears compared to control mice.

Histological Analysis

The head of mice were cut after sacrifice, and then were fixed in Bouin's buffer. After 72 hours, the Bouin's buffer was replaced by PBS containing 14% EDTA (Ethylenediaminetetraacetic acid) to remove calcium at least 72 hours. When the calcium were completely removed, using scissors to cut tissue other than eye ball and conjunctiva. The clipping tissue were then embedded in paraffin, and cut into 5 µm thickness sections. The slices were stained with Giemsa stain (GIEMSA STAIN STOCK SOLUTION, Sigma, USA) Infiltrating eosinophils in the lamina propria mucosae of the conjunctivas throughout each section were counted. The data are presented as an average±S.E.M. per slide of all the mice examined.

Figure 10A:
FIG. 10A is a photograph showing the infiltration of eosinophils into the conjunctiva in normal mice.
Figure 10B:
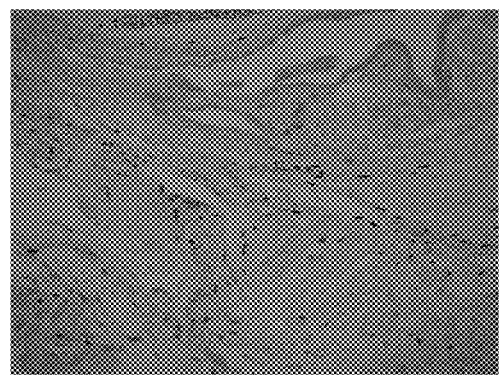
FIG. 10B is a photograph showing the infiltration of eosinophils into the conjunctiva in control mice which is active immunized but no treatment of polysaccharides.
Figure 10C:
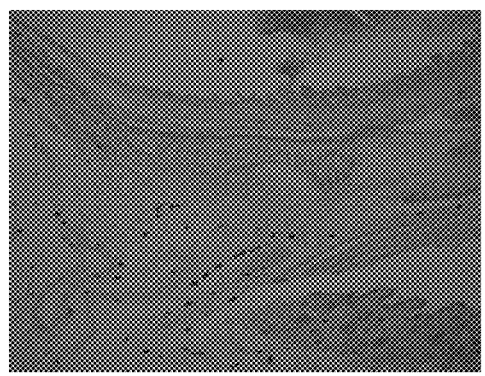
FIG. 10C is a photograph showing the infiltration of eosinophils into the conjunctiva in the active immunized mice which are orally administrated with 30 mg/kg/day of polysaccharides extracted from *Dendrobii Herba*.
Figure 10D:
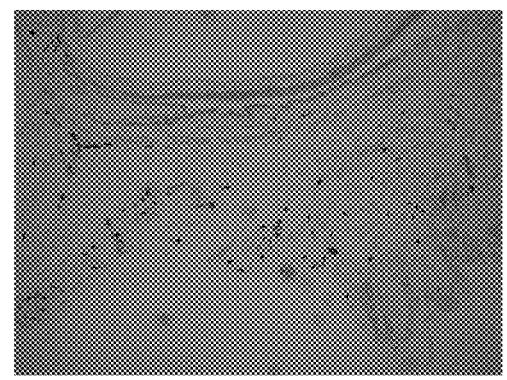
FIG. 10D is a photograph showing the infiltration of eosinophils into the conjunctiva in the active immunized mice which are orally administrated with 30 mg/kg/day of polysaccharides extracted from *Dendrobii Herba*.
Figure 10:
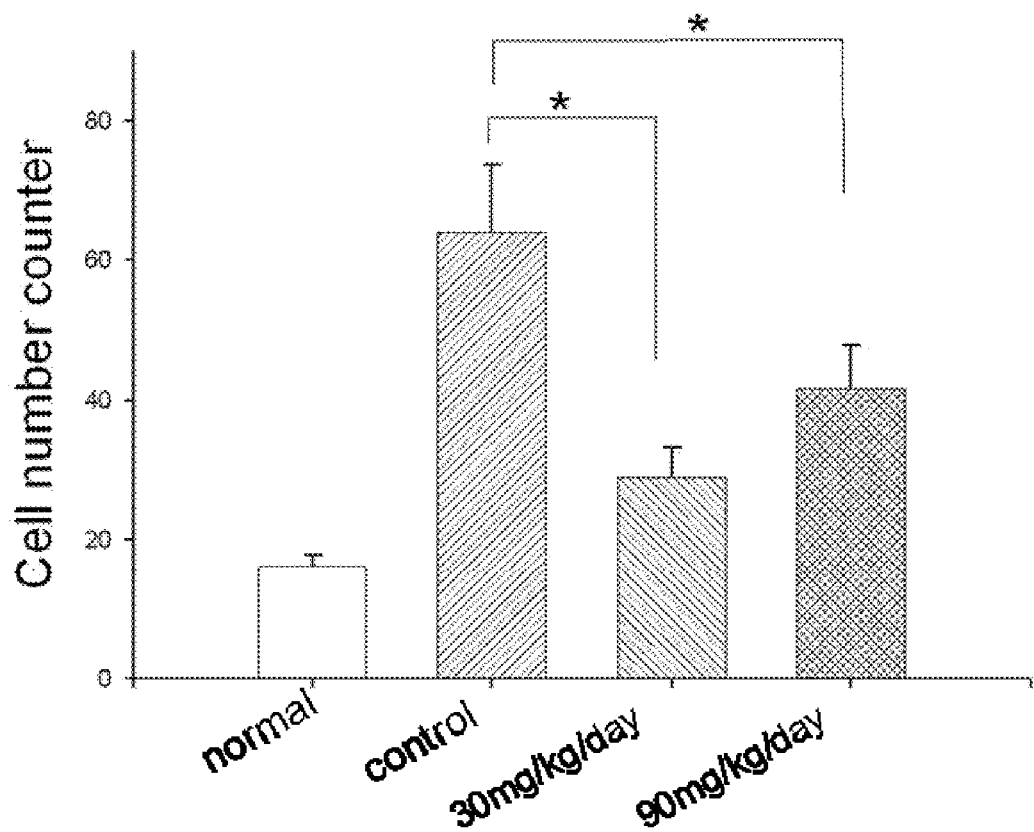
FIG. 10E is a diagram showing the count of infiltrated eosinophils into the conjunctiva. * indicating p<0.05 (compared with the control group).

Eosinophil infiltration into the conjunctiva can be used as a marker for the severity of allergic conjunctivitis, since it has been reported that higher numbers of eosinophils are detected as the severity of allergy increases (Sumi et al., *Int Arch Allergy Immunol.* 143(4):276-81, 2007). As shown in FIG. 10A-D, the control group had the most infiltrating cells. Compared to control group, the number of infiltrating cells significantly decreased in 30 mg/kg/day treatment and 90 mg/kg/day treatment group (FIG. 10E). As the result, it could indicate that with treatment of polysaccharides extracted from *Dendrobii Herba* could relief the severity of allergy.

Measurement of IgE in Serum

On Day 0, 24 and 40 after challenge, the blood of actively immunized mice was collected and serum was prepared. Ragweed pollen-specific IgE levels in the sera were measure by ELSA detailed in aforementioned example.

Figure 11:
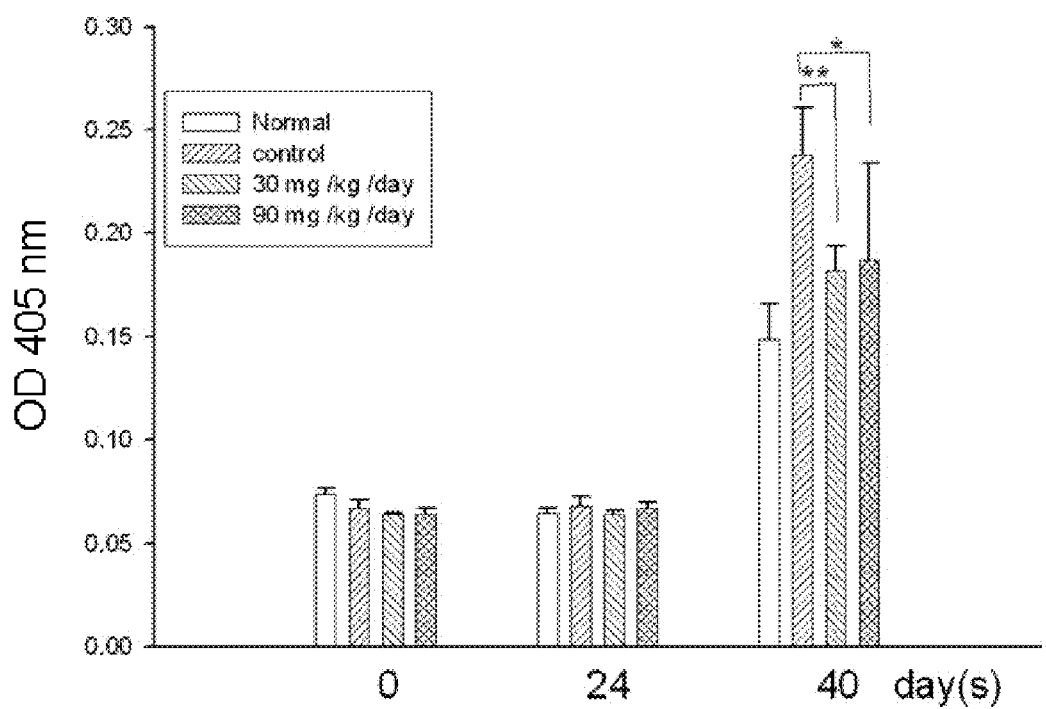
FIG. 11 is a diagram showing Ragweed pollen-specific IgE levels in the serum measured by ELISA on days 0, 24 and 40. The normal group (□) was healthy mice. The control group ▨)was sensitized with Ragweed pollen but without *Dendrobii Herba* treatment. The treatment groups sensitized with Ragweed pollen were fed with a dose of 30 mg/kg/day ▨)and 90 mg/kg/day ▤).* indicating p<0.05, ** indicating p<0.01.

As shown in FIG. 11, on Day 40, the mice of orally administrated with 30 mg/kg/day or 90 mg/kg/day of polysaccharides extracted from *Dendrobii Herba* had significantly lower level of IgE compared to control mice.

Flow Cytometric Analysis

Freshly isolated RBC-depleted splenocytes were fixed with 2% formaldehyde, and washed with FACS buffer (PBS+ 1% fetal calf serum). After the washing, the cells were incubated with Goat FITC-conjugated anti-mouse CD4+ antibody at optimal concentration for 30 min at 4° C., and washed twice with the same buffer. After the washing, the cells were then incubated with Goat PE-conjugated anti-mouse CD25+ antibody at optimal concentration for 30 min at 4☐, and washed twice with the same buffer. Finally, the cells were resuspended with 100 µl FACS buffer and analyzed on a FACScan (Becton Dickinson Bioscience, San Diego, Calif., USA). The analysis and acquisition were performed using CellQuest software.

Figure 12:
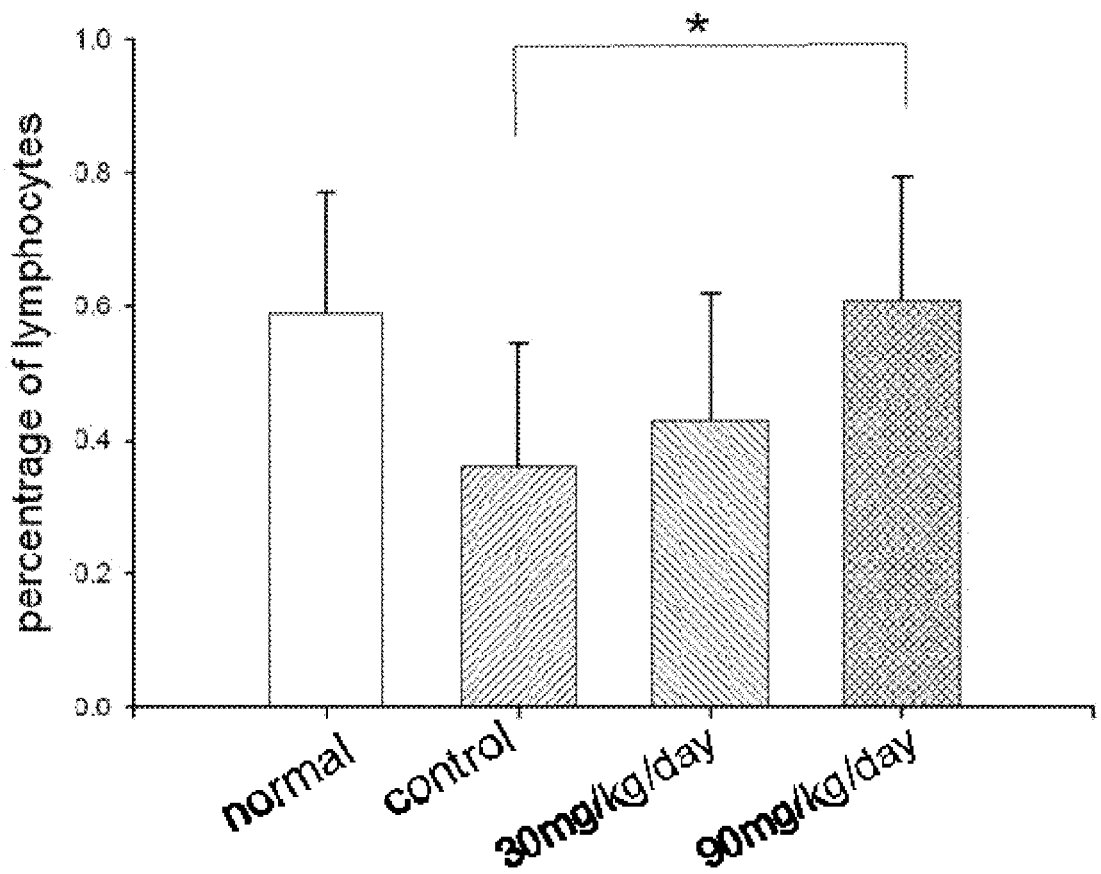
FIG. 12A is a diagram showing the number of CD4+CD25+ T cells in splenocytes by flow cytometric analysis. * indicating p<0.05.
FIG. 12B is a diagram showing the number of CD4+CD25+ T cells in the serum by flow cytometric analysis. * indicating p<0.05.
Figure 12B:
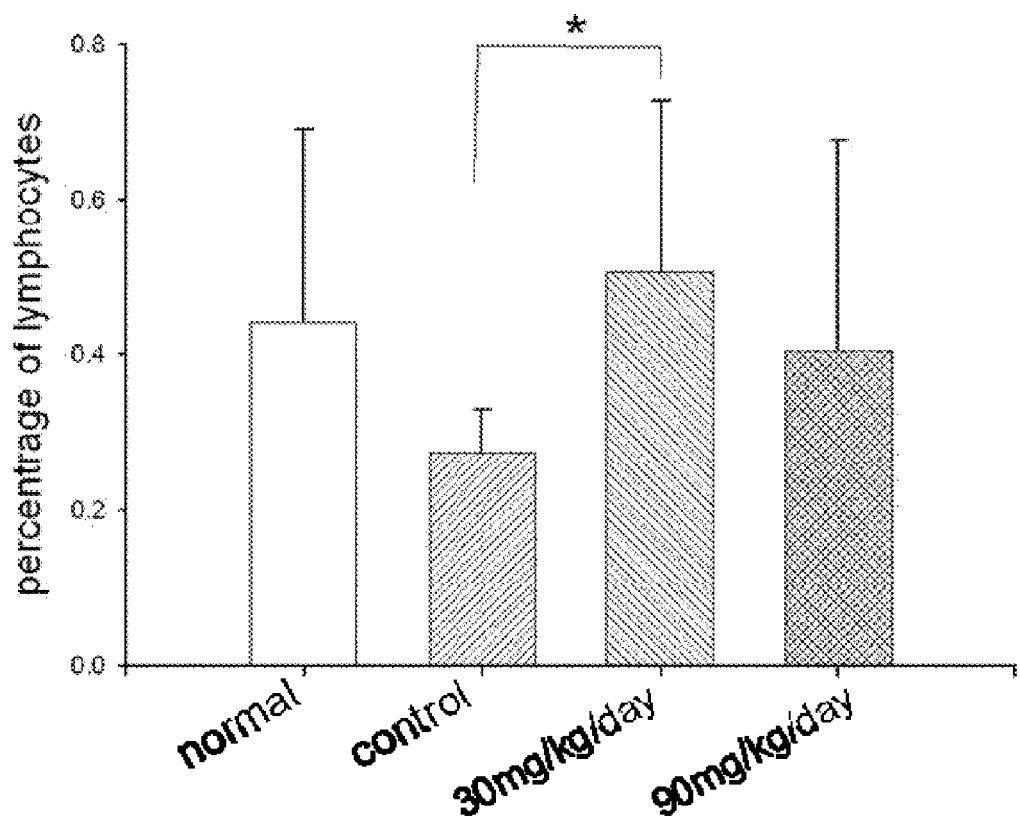

As the result shown in FIG. 12A and FIG. 12B, the percentage of CD4+CD25+ T cells were lower in splenocyte and serum of actively immunized mice. Compared to control mice, those of orally administrated with 30 mg/kg/day or 90 mg/kg/day of polysaccharides extracted from *Dendrobii Herba* had higher percentage of CD4+CD25+ T cells.

Example 4

The Effect of Polysaccharides Extracted from *Dendrobii Herba* on Atopic Dermatitis Set Up Atopic Dermatitis Animal Model On Day 0, nine weeks old of mice was sensitized by applying 100 µl 1% oxazolone to abdominal skin, while PBS group as normal group. On Day 7 and Day 8, 40 µl 0.5% oxazolone was applied topically on both ears. Control group was receiving sensitization and challenge but without polysaccharide treatment. The mice of other groups were orally administrated with 10 mg/kg/day, 30 mg/kg/day or 90 mg/kg/day of polysaccharides extracted from *Dendrobii Herba* respectively four days before the sensitization on Day 0 until sacrificed. The thickness of ears were measured on Day 9 and 10, i.e. twenty-four hours after challenge on Day 8. The data of Day 9 are presented as an average±S.E.M. of all the mice examined.

Result

Figure 13:
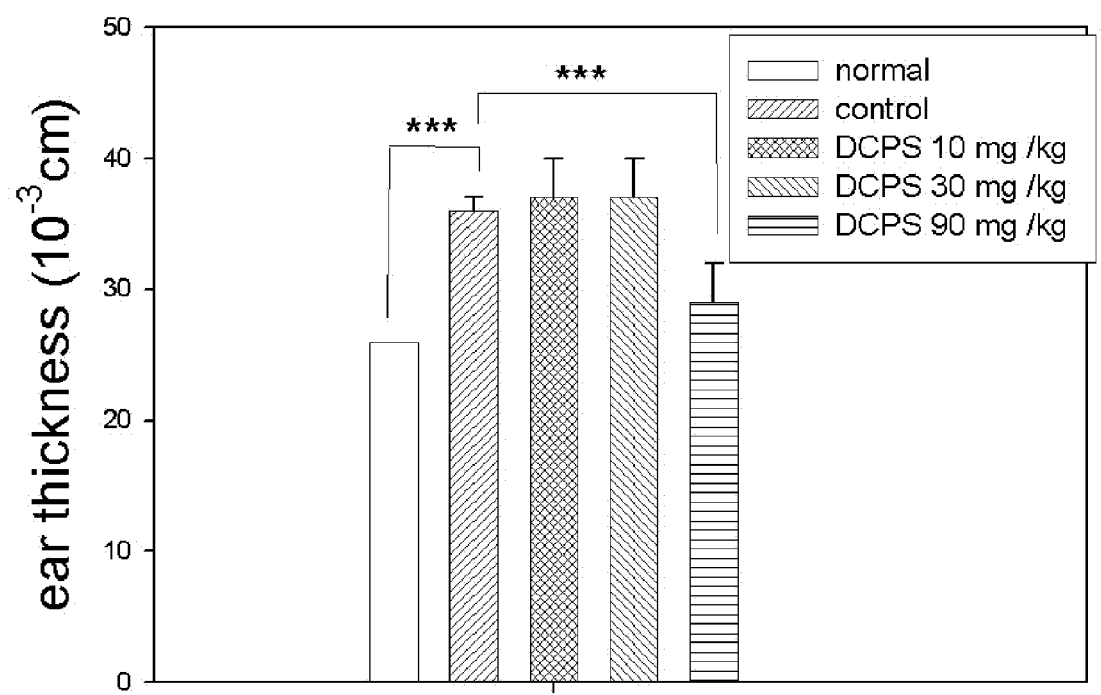
FIG. 13 is a diagram showing the thickness of the ears. The normal group (□) was healthy mice. The control group ▨)was sensitized with 1% ozazolone but without *Dendrobii Herba* treatment. The treatment groups sensitized with 1% ozazolone were fed with a dose of 10 mg/kg/day ⊠)30 mg/kg/day ▨)and 90 mg/kg/day ▤).*** indicating p<0.001.

As the result shown in FIG. 13, the thickness of ears of all mice with active immunized had increased. Compared to control group, 10 mg/kg/day group and 30 mg/kg/day group were no obvious effect; however, the ear thickness of 90 mg/kg/day group significantly decreased.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating an allergic disease, comprising administering to a subject in need thereof an effective amount of polysaccharides obtained from *Dendrobii Herba*.

2. The method of claim 1, wherein the allergic disease is associated with an increased level of eosinophils, IgE, a chemokine, or a Th2 cytokine.

3. The method of claim 1, wherein the allergic disease is asthma.

4. The method of claim 1, wherein the allergic disease is pollen allergy or allergic conjunctivitis.

5. The method of claim 1, wherein the allergic disease is atopic dermatitis.

6. The method of claim 1, wherein the polysaccharides are administered orally.

7. The method of claim 1, wherein the polysaccharides are prepared by a process including:

soaking a first *Dendrobii Herba* preparation in a first alcohol;

removing the first alcohol to produce a second *Dendrobii Herba* preparation;

extracting the second *Dendrobii Herba* preparation with water to obtain an aqueous solution;

mixing the aqueous solution with a second alcohol to allow precipitation of polysaccharides; and collecting the precipitated polysaccharides.

8. The method of claim 7, wherein the first alcohol is methanol, ethanol or a mixture thereof.

9. The method of claim 8, wherein the first alcohol is methanol.

10. The method of claim 7, wherein the second alcohol is ethanol.

11. The method of claim 10, wherein the ethanol has a concentration ranging from 30% (w/v) to 70% (w/v).

12. The method of claim 11, wherein the ethanol has a concentration of 50% (w/v).

13. A method for reducing airway-remodeling caused by inflammation, comprising administering to a subject in need thereof an effective amount of polysaccharides obtained from *Dendrobii Herba*.

14. The method of claim 13, wherein the polysaccharides are administered orally.

15. The method of claim 13, wherein the polysaccharides are prepared by a process including:
    soaking a first *Dendrobii Herba* preparation in a first alcohol;
    removing the first alcohol to produce a second *Dendrobii Herba* preparation;
    extracting the second *Dendrobii Herba* preparation with water to obtain an aqueous solution;
    mixing the aqueous solution with a second alcohol to allow precipitation of polysaccharides; and
    collecting the precipitated polysaccharides.

16. The method of claim 15, wherein the first alcohol is methanol, ethanol or a mixture thereof.

17. The method of claim 16, wherein the first alcohol is methanol.

18. The method of claim 15, wherein the second alcohol is ethanol.

19. The method of claim 18, wherein the ethanol has a concentration ranging from 30% (w/v) to 70% (w/v).

20. The method of claim 19, wherein the ethanol has a concentration of 50% (w/v).

* * * * *